United States Patent [19]
Duan et al.

[11] Patent Number: 6,077,705
[45] Date of Patent: Jun. 20, 2000

[54] RIBOZYME-MEDIATED GENE REPLACEMENT

[75] Inventors: Lingxun Duan, North Wales; Mark A. Zern, Newtown; Roger J. Pomerantz, Chalfont, all of Pa.

[73] Assignee: Thomas Jefferson University, Philadelphia, Pa.

[21] Appl. No.: 08/856,331

[22] Filed: May 14, 1997

Related U.S. Application Data

[60] Provisional application No. 60/017,132, May 17, 1996.
[51] Int. Cl.⁷ .................... C07H 21/04; C12N 15/85; C12Q 1/68
[52] U.S. Cl. .................. 435/320.1; 435/6; 435/93.31; 536/23.1; 536/24.1; 536/24.5
[58] Field of Search .................. 435/6, 172.1, 172.3, 435/69.1, 93.31, 375, 377, 320.1; 536/23.1, 24.1, 24.5; 514/44

[56] References Cited

U.S. PATENT DOCUMENTS 5,399,684   3/1995   Davie et al. ........................ 536/23.5

FOREIGN PATENT DOCUMENTS

WO96/20598-A1   6/1996   WIPO .

OTHER PUBLICATIONS

Cai et al "Suppresion of Lung Cancer Cell Growth by Ribozym–Mediated Modification of p53 pre–mRNA" Cancer Gene Therapy vol. 2(3):199–205, Sep. 1995.
Bollen et al., 1983, DNA 2(4),255–64.
Chomczynski, P, et al., 1987, Anal. Biochem., 162:156–159.
Davis, E.S. et al., 1990, J. Biol. Chem., 265: 22153–22158.
Denman, R.B. 1993, Biotechniques, 15:1090–1094.
Frizell, E. et al., 1995, Hepatology, 21:847–854.
Lee, S.W. et al., 1994 J. Virol. 68:8254–8264.
Mol. Cell. Biol.,1986 6: 2895–2902.
Scharfmann, R. et al., 1991 Proc. Natl. Acad. Sci. USA 88:4624–4630.
Strayer, D.S. and J. Milano 1996 Gene Therapy 3:581–587.
Strayer, D.S. 1996 J. Biol. Chem. 27:24741–24746.
Yun–Tso, J. et al., 1985, Nucl. acid. Res., 13, 2485–2502.
Pierce et al "Construction of a Directed Hammerhead Ribozyme Library: Towards the Identification of Optimal Target Sites for Antisense–Mediated Gene Inhibition" NAR vol. 26(22):5093–5101, 1998.

*Primary Examiner*—John S. Brusca
*Assistant Examiner*—Sean McGarry
*Attorney, Agent, or Firm*—Akin, Gump, Strauss, Hauer & Feld, L.L.P.

[57] ABSTRACT

Methods of gene therapy, particular ribozyme-mediated gene replacement methods, are disclosed. Method of treating patients suffering from a disease associated with expression of an abnormal form of a gene, such as alpha-1 antitrypsin mutations, are disclosed. The methods comprise the steps of administering to such a patient a nucleic acid construct encoding a ribozyme and a nucleic acid construct comprising a ribozyme resistant gene encoding a wild type form of the gene product. Recombinant vectors and pharmaceutical compositions for practicing the methods are disclosed.

4 Claims, 15 Drawing Sheets

```
                    204
        5'-AGCUGGCACACCAGUCCAACAGCACCAAUA-3'    SEQ ID NO. 12
        3'-UCGACCGUGUGGUCA GUUGUCGUGGUUAU-5'    SEQ ID NO. 13
AT204                 A   C
                      A   U
                   A  G   U
                   G GGAC   G
                   C CCUGA   A
                      G   GU 505
        5'-AGAAGCCUUCACUGUCAAGGAGUUGA-3'        SEQ ID NO. 14
        3'-UCUUCGGAAGUGACA UUCCUCGUUCU-5'       SEQ ID NO. 15
AT505                 A   C
                      A   U
                   A  G   U
                   G GGAC   G
                   C CCUGA   A
                      G   GU 589
        5'-AAUUGUGGAUUUGGUCAAGAGCUUGA-3'        SEQ ID NO. 16
        3'-UUAACACCUAAACCA UUCUCGAACU-5'        SEQ ID NO. 17
AT589                 A   C
                      A   U
                   A  G   U
                   G GGAC   G
                   C CCUGA   A
                      G   GU 670
        5'-GAGACCCUUUGAAGUCAAGGACACCGA-3'       SEQ ID NO. 18
        3'-CUCUGGGAAACUUCA UUCCUGUGGCU-5'       SEQ ID NO. 19
AT670                 A   C
                      A   U
                   A  G   U
                   G GGAC   G
                   C CCUGA   A
                      G   GU 777
        5'-ACUGUAAGAAGCUGUCCAGCUGGGUGCUGC-3'    SEQ ID NO. 20
        3'-UGACAUUCUUCGACA GUCGACCCACGACG-5'    SEQ ID NO. 21
AT777                 A   C
                      A   U
                   A  G   U
                   G GGAC   G
                   C CCUGA   A
                      G   GU 918
        5'-AUGAAGACAGAAGGUCUGCCAGCUUACAU-3'     SEQ ID NO. 22
        3'-UACUUCUGUCUUCCA ACGGUCGAAUGUA-5'     SEQ ID NO. 23
AT918                 A   C
                      A   U
                   A  G   U
                   G GGAC   G                   FIG.1
                   C CCUGA   A
                      G   GU
```

```
              Lys Ile Val Asp Leu Val Lys Glu Leu Asp      SEQ ID NO. 24
                              589
wild type: 5'-AAA ATT GTG GAT TTG GTC AAG GAG CTT GAC-3'   SEQ ID NO. 25
modified:  5'-AAG ATAGTC GAC TTAGTG AAA GAA CTA GAA-3'     SEQ ID NO. 26
```

FIG.6

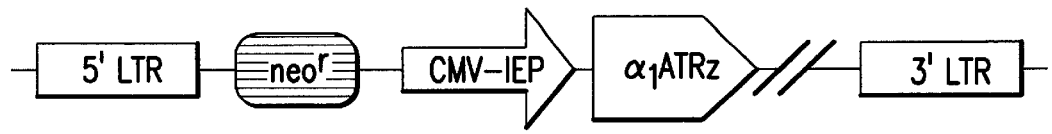
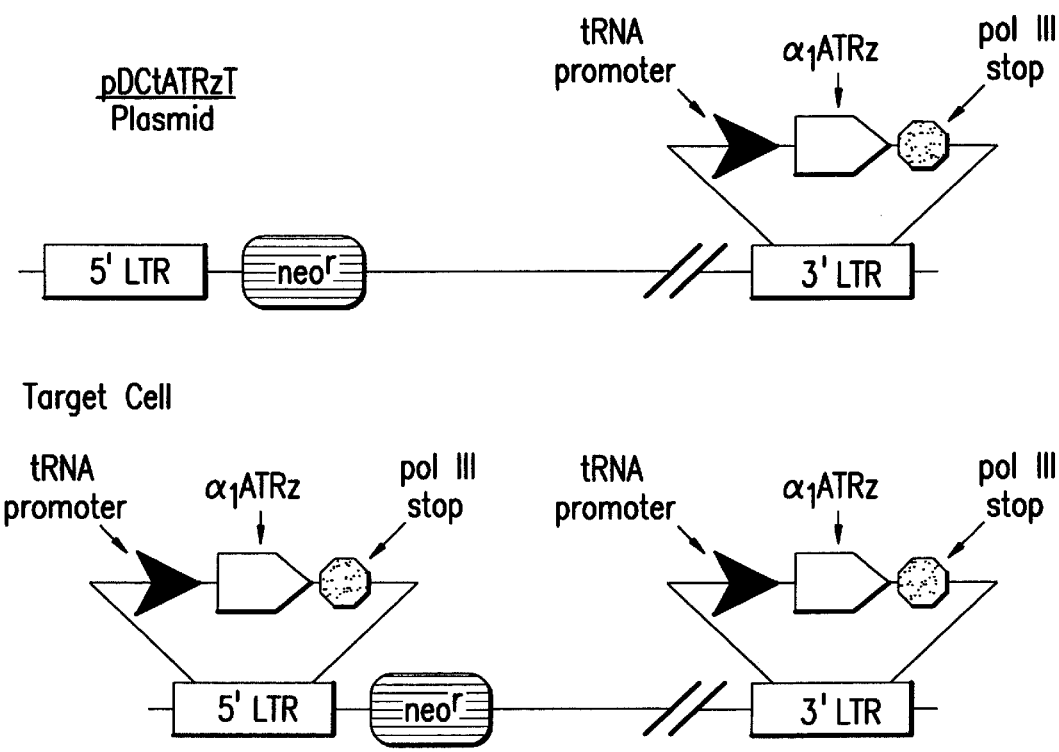
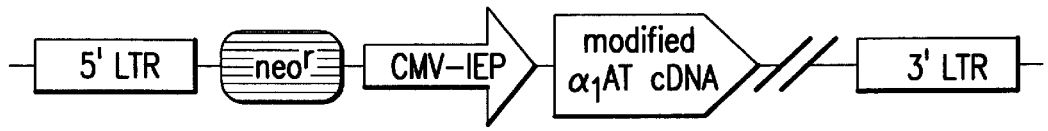

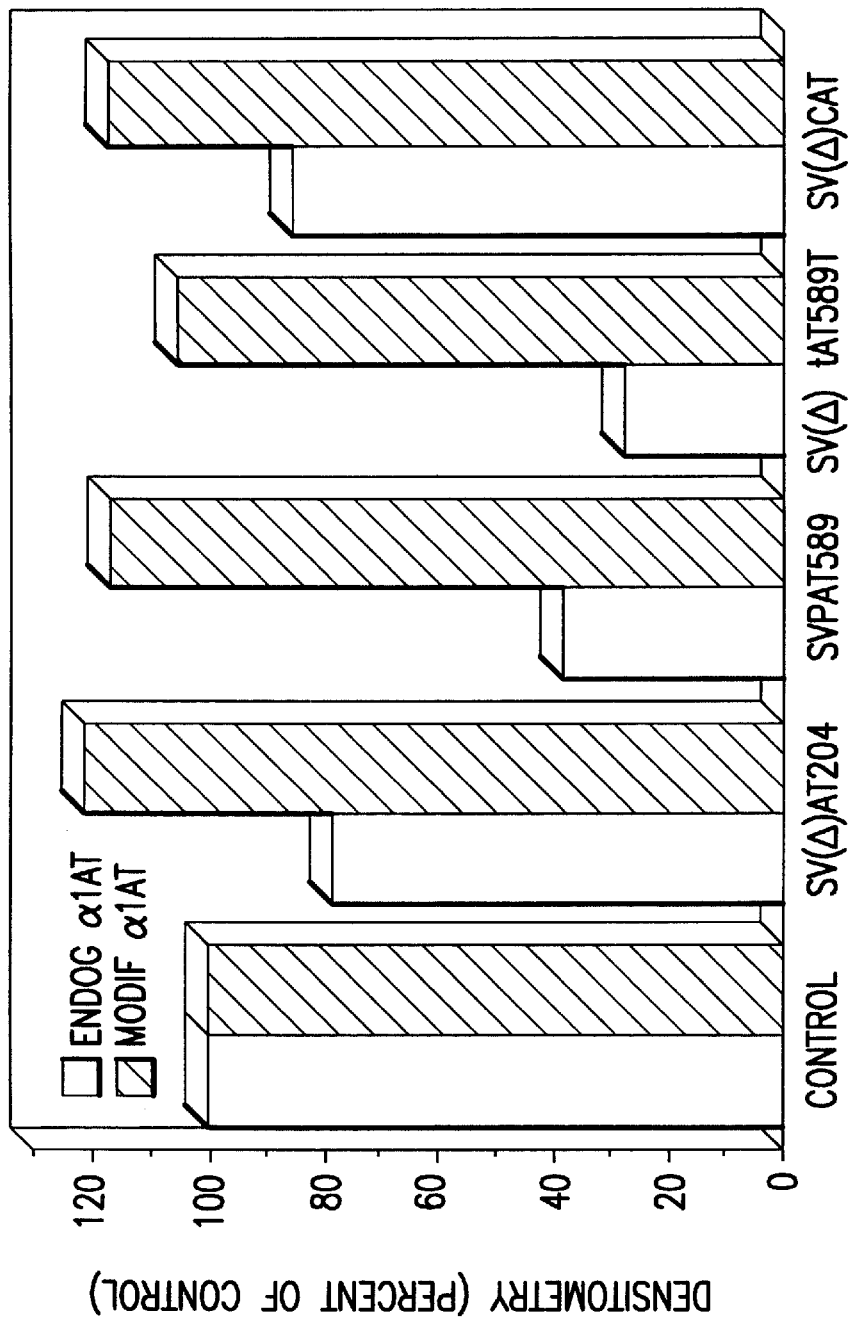

RIBOZYME-MEDIATED GENE REPLACEMENT

CROSS REFERENCE TO RELATED APPLICATIONS

This application claims benefit of U.S. Provisional Application Ser. No. 60/017,132 filed May 17, 1996.

GOVERNMENT SUPPORT

This work was supported in part by USPHS grants AA06386, NS30916, AI33810, AI36552 and AI31836. The U.S. government may have certain rights in the invention.

FIELD OF THE INVENTION

The present invention is directed to human somatic cell gene therapy.

BACKGROUND OF THE INVENTION

Alpha 1-antitrypsin (α1AT)[3] deficiency, one of the more common lethal hereditary disorders in Caucasians of European descent, is characterized by reduced serum levels of α1AT, a 52-kD glycoprotein that functions as an antiprotease. The deficiency state is caused by mutations of the α1AT gene, a pleiomorphic, 12.2-kb 7-exon gene. Normal α1AT serum levels are 20–53 µM; various combinations of at least 17 different mutations of the α1AT gene are associated with an α1AT level <11 µM and significant risk for developing emphysema. A subset of mutations is associated with hepatitis and cirrhosis. These latter mutations all involve the production of abnormal proteins: they do not include null mutations. The pathogenesis of the liver disease is thought to be due to the accumulation of an abnormal α1AT protein in hepatocytes, and is associated with the finding that certain mutations of the α1AT gene cause derangement in the protein's intracellular processing and defects in the protein's excretion, commonly associated with liver injury. The molecular defect in the protease inhibitor (Pi)Z allele, the allele most commonly associated with liver injury, is a G to A transition resulting in a Glu to Lys substitution at amino acid 342. This mutation is thought to cause the variant protein to aggregate in the rough endoplasmic reticulum of the liver cells.

In the field of gene therapy, "gene replacement" is a useful approach. "Gene replacement" refers to the replacement of a mutated genetic element with a normal gene.

Ribozymes are RNA molecules which have the ability to cleave RNA sequences at specific sites. The hammerhead ribozyme motif, first identified in the self-splicing activity of a plant RNA virus, cleaves the phosphodiester bond downstream of a GUX triplet, where X can be C, U, or A. Target specificity for this cleavage can be achieved by flanking the hammerhead ribozyme motif with antisense sequences, complementary to the target RNA. Ribozymes have been targeted to a wide variety of substrates and tested in biological systems to achieve the inhibition of cellular gene expression or viral replication.

There is a need for providing improved methods of gene replacement therapy. There is a need for compositions and methods for treating individuals who have alpha 1-antitrypsin deficiency.

SUMMARY OF THE INVENTION

The present invention relates to methods of treating patients who have diseases associated with expression of an abnormal form of a gene. The methods comprise the step of administering to such a patient a nucleic acid construct that encodes a ribozyme and a nucleic acid construct that comprises a ribozyme resistant gene encoding a wild type form of the abnormal gene product.

The present invention relates to nucleic acid constructs, combinations of constructs, and vectors that comprise such constructs and combinantions of constructs.

The present invention provides recombinant viral vectors that include nucleic acid constructs that encode a ribozyme and nucleic acid constructs that comprises a ribozyme resistant gene encoding a wild type form of the abnormal gene product.

The present invention provides pharmaceutical compositions that comprise nucleic acid constructs, combinantions of constructs and vectors that comprise such constructs and combinantions of constructs.

In some embodiments of the present invention, methods, nucleic acid molecules, and recombinant vectors are provided for treating patients who have diseases associated with expression of an abnormal form of alpha-1 antitrypsin.

BRIEF DESCRIPTION OF THE FIGURES

FIG. 1 illustrates the sequences of targeted human α1-AT mRNA and the predicted structures of ribozyme AT204 (SEQ ID NO:12 and SEQ ID NO:13), AT505 (SEQ ID NO:14 and SEQ ID NO:15), AT589 (SEQ ID NO:16 and SEQ ID NO:17), AT670 (SEQ ID NO:18 and SEQ ID NO:19), AT777 (SEQ ID NO:20 and SEQ ID NO:21) and AT918 (SEQ ID NO:22 and SEQ ID NO:23).

FIG. 2A shows ribozyme cleavage products of ribozyme AT505. AT505 ribozyme (118 base) labeled with [a-$^{32}$P]UTP cleaved α1-AT RNA (S) into two fragments, P1 (5'-cleavage product of 268 bases) and P2 (3'-cleavage product of 172 bases). Lane 1) Substrate RNA; Lane 2) AT505 ribozyme; Lane 3) Incubation products of the substrate and AT505. FIG. 2B shows ribozyme cleavage products of ribozyme AT589. AT589 ribozyme (124 bases) cleaved α1-AT RNA (S) into two fragments, P1 (5'-cleavage product of 352 bases) and P2 (3'-cleavage product of 88 bases). Lane 1) Substrate RNA; Lane 2) AT589 ribozyme; Lane 3) Incubation products of substrate RNA and AT589.

FIG. 4A shows Northern blot hybridized with α1-AT probe. Lane c: transduced PLC/PRF/5 cells with anti-mouse IgG kappa chain ribozyme as control; Lane AT204: Cells transduced with AT204 ribozyme; Lane AT505: Cells transduced with AT505 ribozyme; Lane AT589: Cells transduced with AT589 ribozyme. Lane AT670: Cells transduced with AT670 ribozyme, Lane AT777: cells transduced with AT777 ribozyme, Lane AT918: cells transduced with AT 918 ribozyme. FIG. 4B is the same blot re-hybridized with GAPDH probe.

FIG. 5A shows RNA samples hybridized with α-AT probe and FIG. 5B shows the same blot hybridized with GAPDH probe.

FIG. 5C shows transduced cell proteins separated on 10% SDS-PAGE and probed with rabbit anti-human α1-AT antibody. FIG. 5D shows the same blot probed with rabbit anti-human b-actin antibody.

Lane c: PLC/PRF/5 cells transduced with anti-mouse IgG kappa chain ribozyme (ABVK) as control. lanes 1–6 present 6 individual single cell clones transduced with retroviral vector carrying AT589 ribozyme (pDCt2AT589T).

FIG. 6 is a schematic representation of the amino acid sequence (SEQ ID NO:24) and comparison of the nucleotide sequences of human wild-type (upper panel—SEQ ID NO:25) and modified (lower panel—SEQ ID NO:26) α1-AT cDNA.

Figure 7:

FIG. 7 is a Northern blot of mRNA expression of α1-AT, GAPDH, and the ATS89 ribozyme in PLC/PRF/5 cells transduced with the pSLXCMVmα1AT-t2AT589T retroviral vector. X represents cellular endogenous α1-AT mRNA; Y is modified α1-AT mRNA from retroviral vector transcription; Z is the α1-AT mRNA transcripted from the bi-functional pSLXCMVmaAT-tAT589T retroviral vector. Lane 1: cells transduced with pSLXCMVmαAT; Lane 2: cells transduced with ABVK control ribozyme; Lane 3: cells transduced with bi-functional pSLXCMVma1AT-t2AT589T.

Figure 8:
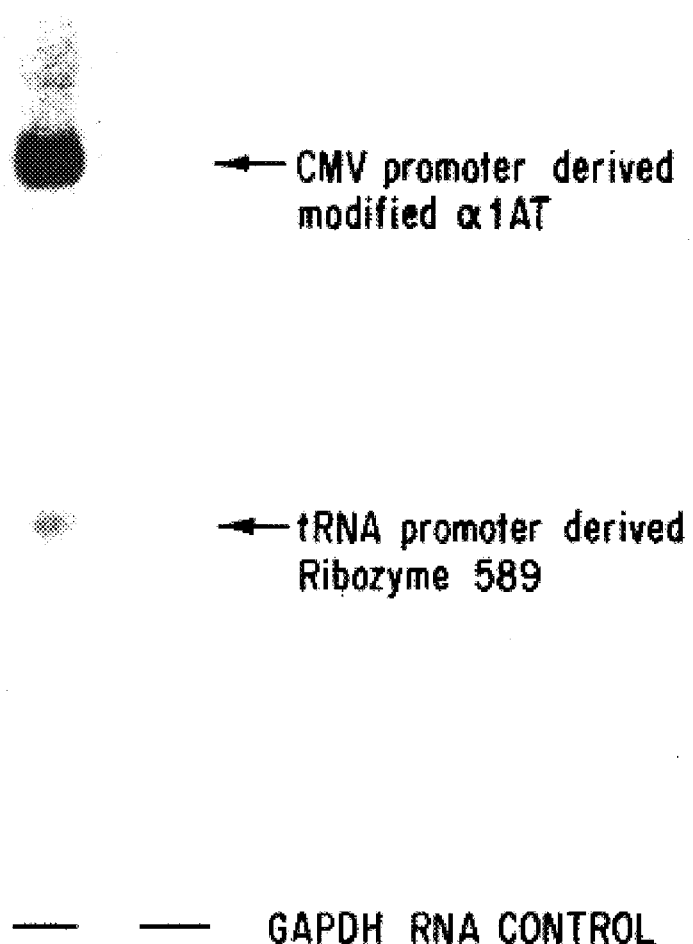

FIG. 8 is a Northern blot of inserted genes' RNA expression analysis from AG cells transduced with the bifunctional pSLXCMVmaAT-tAT589T retroviral vector. Lane 1: transduced AG 5199 cells. A: modified α1-AT mRNA which transcripted from internal CMV promoter. B: tRNA promoter derived ribozyme AT589 RNA transcripts. Lane 2: un-transduced AG 5199 cells.

FIGS. 9A, 9B and 9C depict the structure of retroviral vectors that express the α1AT ribozyme (ATRZ) from either a CMV promoter (FIG. 9A; pSLXCMVATRzs) or a tRNA promoter cassette with an RNA polymerase III termination signal (FIG. 9B; pDCtATRzsT). In the target cell, the tRNA-ATRz template is duplicated and transferred to the 5'-LTR ("double copy") vector). (FIG. 9C): Structure of the retroviral vector that expresses the modified α1AT cDNA. Arrow shows the direction of transcription.

Figure 10:
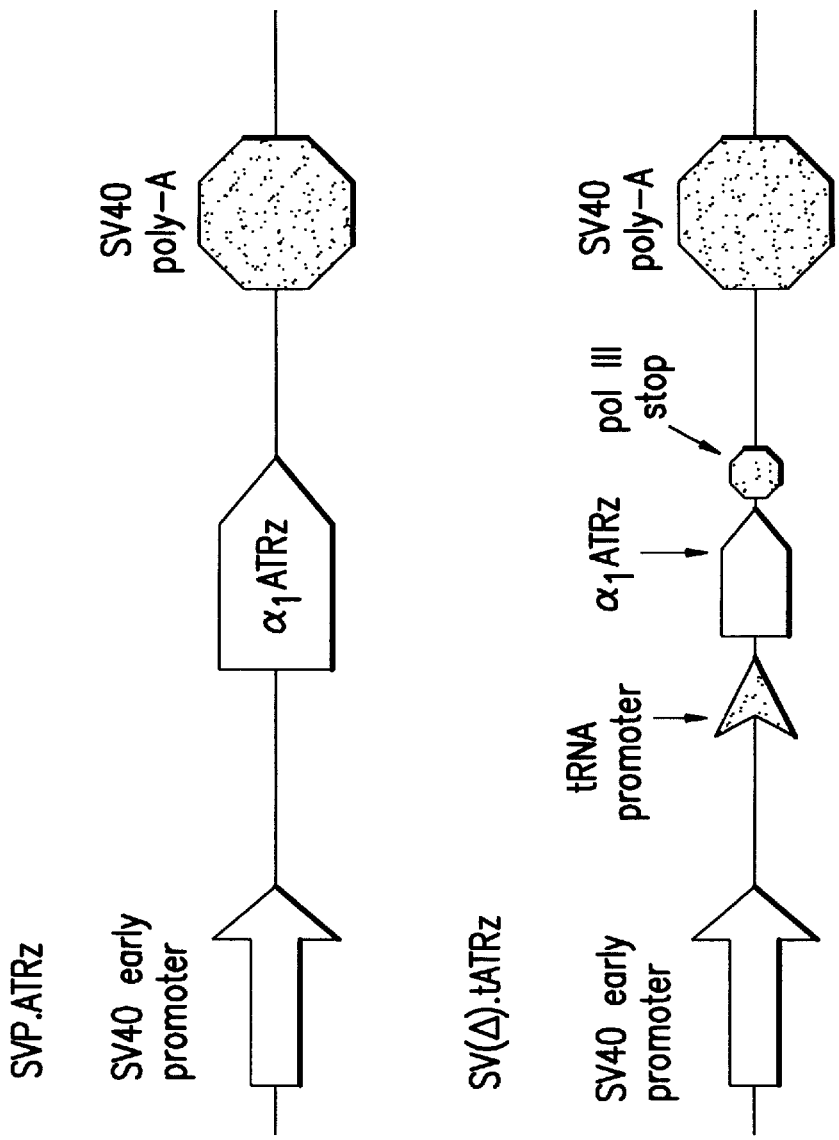

FIG. 10 depicts the structure of SV40 vectors that express the α1AT ribozyme from either the SV40 early promoter [SVP.ATRz], or from a tRNA promoter cassette [SV(Δ).tATRz].

Figure 11:
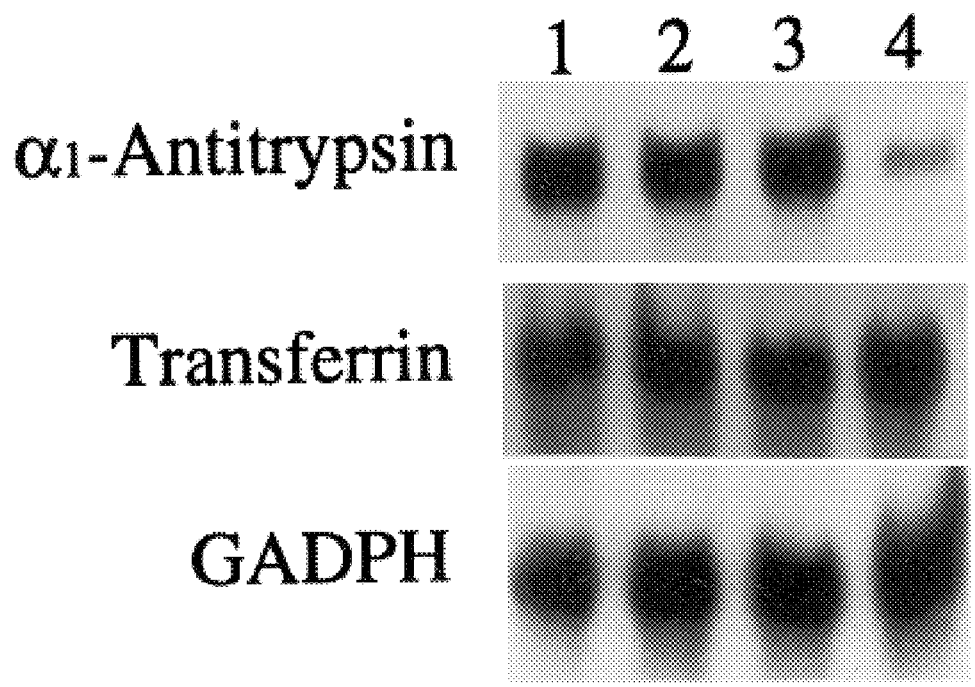

FIG. 11 presents a representative Northern blot of RNA extracted from a pooled population of PLC/PRF/5 cells that were untransfected (lane 1), or transduced with a control ribozyme, anti-mouse IgG kappa chain (lane 2), or a retroviral vector containing an α1AT ribozyme driven by a CMV promoter (pSLXCMVAT589) (lane 3), or a tRNA promoter (pDCt2AT589T) (lane 4), then selected with G418. The RNA was electrophoresed then hybridized with either an α1AT, GAPDH, or transferrin cDNA probe as described in Materials and Methods section of Example 10.

Figure 12:
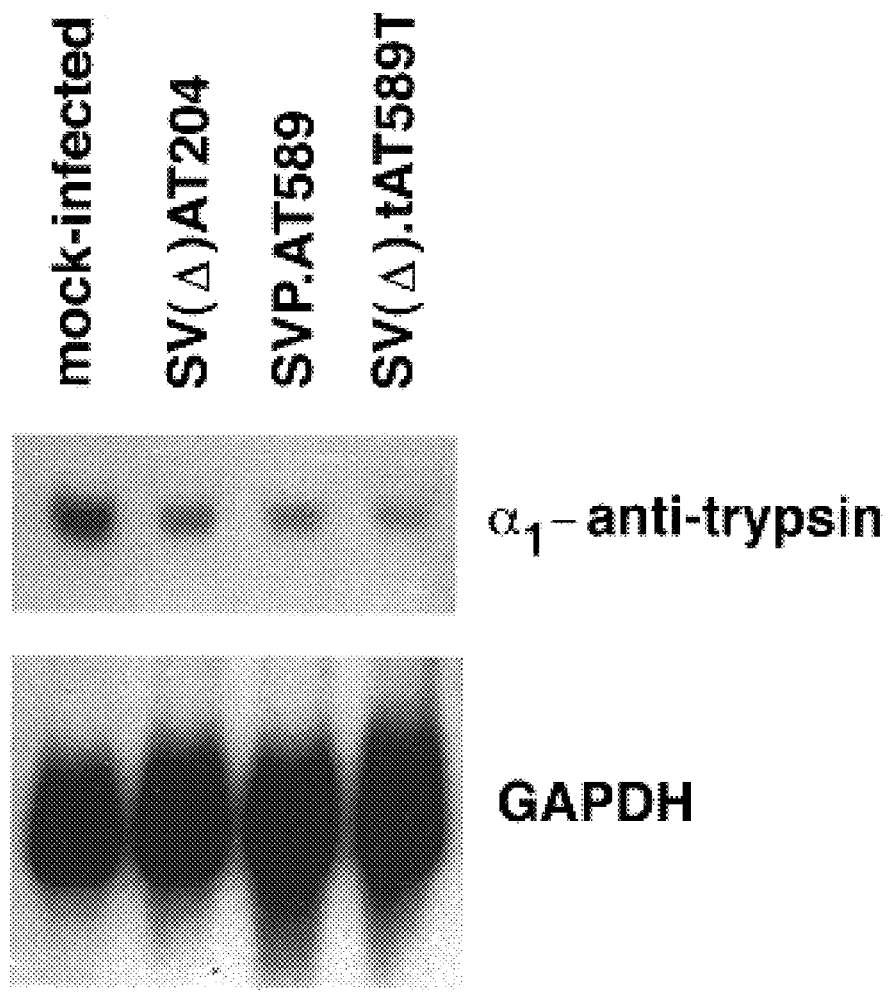

FIG. 12 presents a representative Northern Blot of RNA extracted from an unselected population of PLC/PRF/5 cells that were mock-infected or infected 48 hours previously with an SV40-derived vector containing an α1AT ribozyme driven by either the SV40 early promoter (SVP.AT589) or by a tRNA promoter [SV(Δ)AT204] or [SV(Δ).tAT589T]. The RNA was electrophoresed, then hybridized with α1AT or GAPDH probes as described in Materials and Methods section of Example 10.

Figure 13:
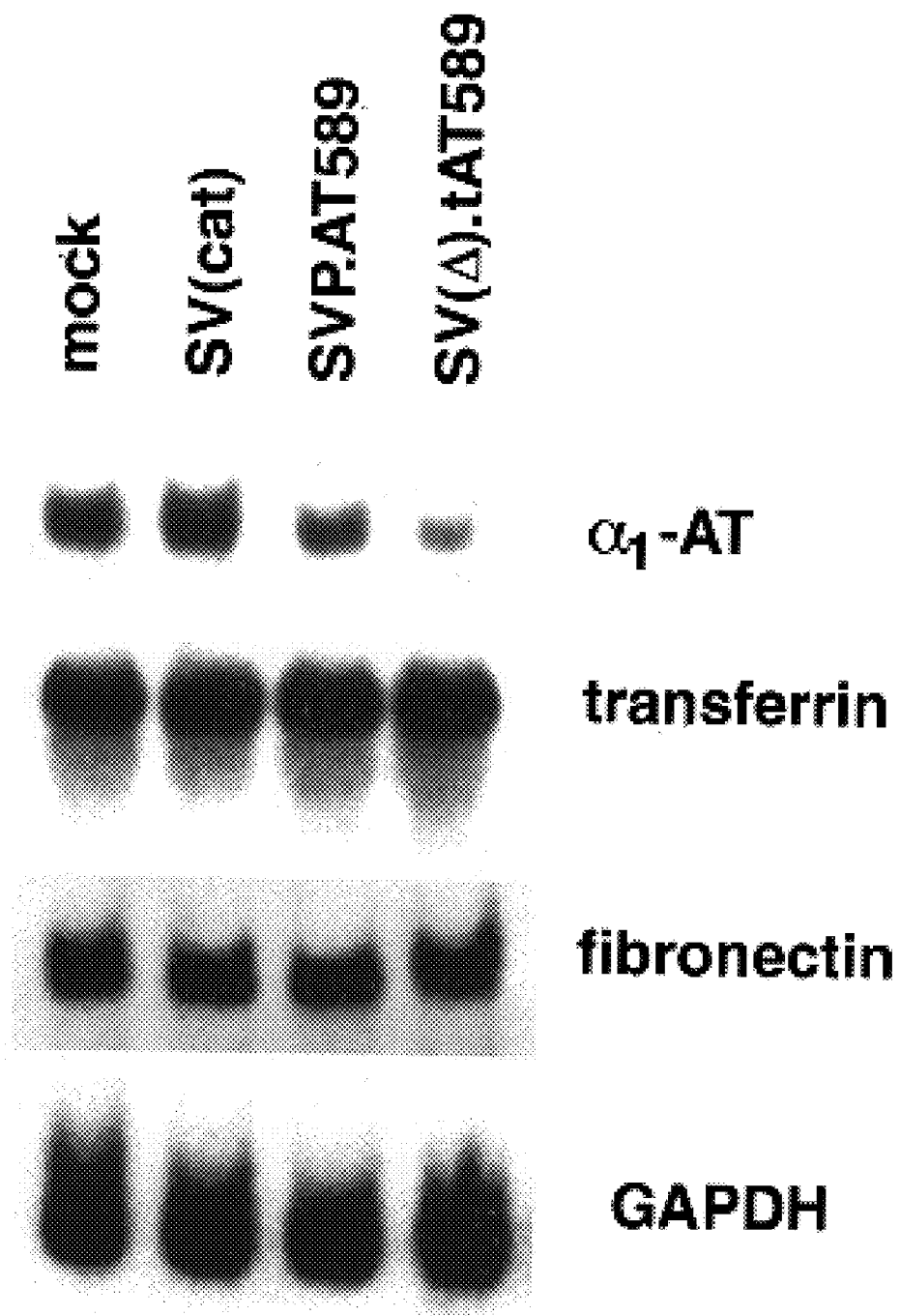

FIG. 13 presents a Northern blot hybridization analysis of α1AT ribozymes employing an SV-40 vector system. PLC/PRF/5 cells were infected in culture, with SV(Δ)CAT, BSVP.AT589, or BSV(Δ).AT589T at moi ~100, or they were mock-infected. Cells were infected and RNA extracted as per Materials and Methods. SV(Δ)CAT represents a control for transduction.

Figure 14A:
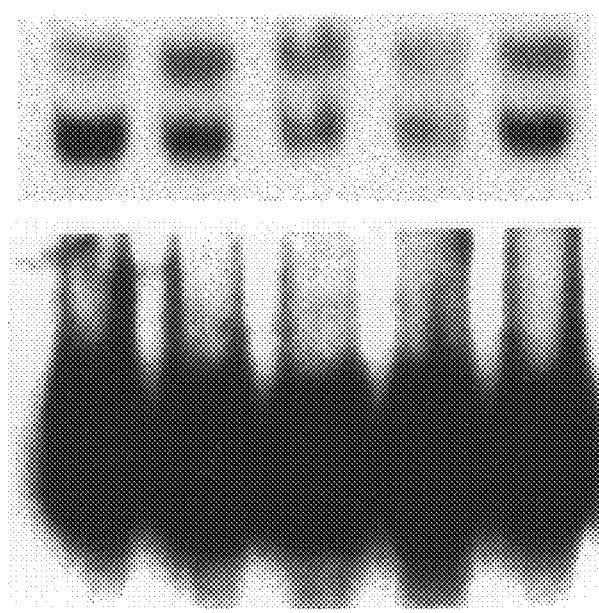

FIG. 14A present a Northern blot hybridization analysis of the effects of α1AT ribozymes on the expression of endogenous and modified α1AT in PLC/PRF5 cells. The hepatoma cell line was stably transduced with pSLXCMVmα1AT which led to expression of the modified α1AT, then transduced with SV-40 virus at moi ~100. Lane 1, untransduced cells; Lane 2, cells transduced with SVP.AT204; Lane 3, transduced with SVP.AT589; Lane 4, SV(Δ).tAT589T; SV(Δ)CAT, in lane 5, represents a control for transduction. Pooled cells from whole cultures were used, and RNA extracted 48 hours after the second transduction.

FIG. 14B is data from densitometry tracing of FIG. 14A, showing effect of ribozymes on endogenous and modified α1AT levels.

DETAILED DESCRIPTION OF THE INVENTION

The present invention provides methods of gene therapy. Specifically, the present invention is a "gene replacement" therapy. Generally the present gene replacement method involves inhibition of an abnormal gene product coupled with replacement with the normal gene. This is particularly important in conditions where the abnormal gene is overexpressed. Generally, methods of the present invention can be used to treat conditions associated with cellular proteins which, when expressed in a mutant form, form dimers or tetramers with the wild type form, resulting in mutant dominant inhibition.

According to one preferred embodiment of the invention, compositions and methods are provided which may be used to treat individuals who have abnormal α1-antitrypsin deficiency. The compositions and methods of the present invention may be used to inhibit the expression of abnormal α1-antitrypsin (α1-AT) and to replace the abnormal α1-AT gene with a normal α1-antitrypsin gene.

Other conditions which may be treated according to the present invention are those associated with overproduction of mutant forms of proteins in which the protein deficiency and the presence of the mutant form are causative of the pathological condition. Examples include conditions associated with mutant p53, ras and PCR1.

By normal gene is meant any gene which, when encoded produces a biologically active, wild-type protein. By abnormal or mutant gene is meant any gene which, when encoded, does not produce a biologically active, wild-type protein. Abnormal gene products may interefere with normal function or lack the ability to confer normal function to a biological system or organism.

To prevent inhibition of the normal gene of interest, methods of the present invention provide for modification of the normal gene using one or more degenerate codons coding for appropriate amino acids, thereby making the normal gene resistant to the gene inhibitor acting on the abnormal gene, while retaining the biological activity of the expressed protein. For instance, the α1-antitrypsin wild type gene can be modified by altering the nucleotide sequence at the ribozyme target site using a degenerate codon so as to preserve normal function of the expressed protein. The wild type cDNA sequence of α1-antitrypsin is described in U.S. Pat. No. 5,399,684 issued Mar. 21, 1995 and Bollen et al., 1983, *DNA*, 2(4), 255–64, both of which are incorporated by reference herein in their entirety. In some embodiments of the present invention at least the GTC codon must be modified although it may be necessary to modify flanking codons as well.

Inhibition of the abnormal gene of interest is achieved, in methods of the invention, by transfection of cells with an expression vector containing a regulatory cassette. In preferred methods of the present invention the regulatory cassette comprises a gene coding for a site specific hammerhead ribozyme targeted to the abnormal gene mRNA. Replacement of the abnormal gene with the associated normal gene and expression of the normal gene product is performed by transfecting cells with an expression vector containing a structural cassette. The structural cassette comprises a modified gene coding for the normal gene product. In some methods of the present invention the expression vector is bifunctional and contains both the regulatory cassette and the structural cassette.

The term "DNA construct" as used herein refers to any DNA molecule which has been modified such that the nucleotide sequences in the molecule are not identical to a sequence which is produced naturally.

The term "expression vector", as used herein, is defined as a DNA construct which includes an autonomous site of replication, a site of transcription initiation, and at least one structural gene coding for a protein which is to be expressed in a host organism. The expression vector will usually also contain appropriate control regions such as a promoter and terminator which control the expression of the protein in the host organism. Expression vectors of the present invention may include retroviral vectors such as the "double copy" vector. As one skilled in the art would recognize, the particular vector chosen depends partly upon the cell-type targeted.

In preferred embodiments of the present invention the expression vector includes a promoter. Vectors encoding one or more ribozymes should preferably utilize a strong, RNA polymerase III type promoter. Useful promoters include, but are not limited to tRNA and SV40 promoters.

Expression vectors of the present invention may also include homologous sequences with a host gene to provide for integration of the modified gene into the chromosome of the host.

The term "bifunctional expression vector" as used herein is defined as an expression vector which contains at least one structural gene cassette coding for a protein which is to be expressed in a host organism and a regulatory cassette coding for a regulatory element. The regulatory cassette may code for any element which functions within the cell to inhibit the expression of one or more genes. In accordance with preferred embodiments of the present invention the regulatory cassette codes for an RNA fragment having ribozyme activity effective to cleave a separate RNA molecule.

Cassette, as used herein, refers to a discrete DNA fragment that encodes a control region and a DNA sequence of interest such a structural protein.

The term "plasmid" is used herein in accordance with its commonly accepted meaning, i.e. autonomously replicating, usually close looped, DNA.

"Ribozyme" as the term is used herein, refers to an enzyme which is made of RNA. Ribozymes are involved in the cleavage and/or ligation of RNA chains. In preferred embodiments of the present invention, "hammerhead ribozymes" are used. As described above, hammerhead ribozymes cleave the phosphodiester bond of a target RNA downstream of a GUX triplet where X can be C, U, or A. Hammerhead ribozymes used in methods of the present invention have a structural domain having the sequence 3'-CAAAGCAGGAGCGCCUGAGUAGUC-5' (SEQ ID NO:1, reported in 5'-3' direction). Site specific regulatory elements such as site specific ribozymes are provided in accordance with the present invention. The ribozyme regulatory element is made site specific, having the sequence 3'-$X_n$-CAAAGCAGGAGCGCCUGAGUAGUC-$Y_m$-5' (SEQ ID NO:1, reported in 5' to 3' direction) where X and Y are complementary to regions of the target mRNA flanking the GUC site and n+m are generally from about 20 to about 35 RNA bases in length. n+m need not be of equal lengths although it is preferable that neither n nor m is less than about 10.

Hammerhead ribozymes target the triplet GUC. For a gene of interest a target site can be identified by analyzing the gene sequence to identify GUC triplets. Computer analysis of secondary structure may assist in site selection. Denman, (1993), *Biotechniques*, 15, 1090–1094.

As used herein, the terms "delivery components" and "vectors" are used interchageably and are meant to refer to vehicles by which nucleic acid molecules may be delivered to cells of an individual.

As used herein, the term "normal, ribozyme-resistant genes" is meant to refer to any nucleic acid molecule, such as RNA and cDNA, that encodes the normal protein but that has an RNA sequence or is transcribed into RNA that is resistant to ribozyme degradation.

The present invention provides ribozymes which degrade mutant gene transcripts. Additionally, the present invention provides normal genes that encode the protein of which the individual has a deficiency but which are resistant to degradtion by the ribozyme. The ribozymes and normal, ribozyme-resistant genes are provided in combination with delivery components such that upon administration of the combination, the ribozyme and ribozyme-resistant normal gene are delivered to cells of the individual. When provided as a pharmaceutical composition, the combination is useful for the treatment of individuals suffering from genetic diseases.

According to one aspect of the invention, ribozymes which degrade RNA transcripts that encode mutant α1-AT are provided. The present invention provides normal, ribozyme resistant genes that encode normal α1-AT but which are not cleaved by the ribozymes. The ribozymes and normal, ribozyme-resistant genes are provided in combination with delivery components such that upon administration of the combination, the ribozyme and ribozyme-resistant normal gene are delivered to cells of the individual. When provided as a pharmaceutical composition, the combination is useful for the treatment of individuals suffering from diseases and conditions associate with α1-AT mutations.

The ribozymes and normal, ribozyme-resistant genes are used in combination with a variety of delivery components, such as recombinant viral expression vectors or other suitable delivery means, so as to affect their introduction and expression an individual's cells. Vectors of the present invention may be delivered to a patient via methods known in the art. In general, viral vectors may be DNA viruses such as recombinant adenoviruses, recombinant SV40 and recombinant vaccinia viruses or RNA viruses such as recombinant retroviruses. In addition to recombinant vectors, other delivery components are also contemplated. The invention is intended to include such other forms of expression vectors and other suitable delivery means which serve equivalent functions and which become known in the art subsequently hereto.

In some embodiments, retroviral mediated delivery is preferred. In vivo delivery by of retroviral vectors may be achieved, for example by i.v. injection of the retroviral vectors. A double balloon catheter may also be used for direct delivery of retroviral vectors to the patient.

In some preferred embodiments constructs are deivered using SV40 vectors as described in PCT/US95/17065, which is incorporated herein by reference.

Pharmaceutical compositions according to the invention include delivery components in combination with ribozymes and normal, ribozyme-resistant genes and a pharmaceutically acceptable carrier or diluent. In some preferred embodiments, SV40 vectors which include sequences for ribozymes that degrade mutant α1-AT transcripts and coding sequences that encode normal, ribozyme-resistant α1-AT genes. Preferred pharmaceutical compositions additionally comprise a pharmaceutically acceptable carrier or diluent.

Pharmaceutical compositions may be formulated by one having ordinary skill in the art with compositions selected depending upon the chosen mode of administration. Suitable pharmaceutical carriers are described in *Remington's Pharmaceutical Sciences*, A. Osol, a standard reference text in this field, which is incorporated herein by reference.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The following examples are illustrative but are not meant to be limiting of the present invention.

EXAMPLES

Example 1
Ribozyme Design and Cloning

The sequences of the targeted human α1-AT mRNA and the designs of ribozymes are illustrated in FIG. 1. As the target sites for ribozymes, several GUC sequences in the human α1-AT mRNA had been chosen, utilizing a computer-assisted program for the prediction of the secondary structure of RNA molecules. Denman, R. B. (1993), *Biotechniques*, 15, 1090–1094. The numbers in FIG. 1 indicate the nucleotide position of the first G of the target GUC triplet when the first A of the initiation codon AUG is numbered as 1. For the design of trans-acting α1-AT ribozymes, designated AT204, AT505, AT589, AT670, AT777 and AT918 respectively, 11 to 14 bases of each antisense arm sequence (against α1 mRNA were flanked on both sides of the hammerhead motif to allow the ribozyme to associate specifically with α1-AT mRNA through their complementary sequences. For the construction of the ribozyme, two complementary oligonucleotides were synthesized. The ribozyme DNA fragments were synthesized by incubating 1 μg of two oligonucleotides to form a hemiduplex, then PCR amplifications were performed in a 100 μl volume containing 10 mM Tris-HCl (pH 8.3),50 mM KCl, 2.5 mM MgCl$_2$, 200 μM of each dNTP, and 5 Units of Taq DNA polymerase (Perkin-Elmer, Branchburg, N.J.). The cycling conditions were as follows: 94° C. for 1.5 min, 50° C. for 1.5 min, and 72° C. for 2 min for 10 cycles. Then PCR products were directly cloned into the pT7BIue-T vector (Novagen, Madison, Wis.) to generate plasmid pT7ATRzs, which contains each ribozyme under the control of the bacteriophage T7 promoter. Although, in vitro, all of the constructed ribozymes could cleave the target α1-AT RNA at the specific sites in a cell free cleavage system, there were some differences in terms of cleavage efficiency among these α1-AT ribozymes. As examples of ribozyme mediated cleavage of α1-AT RNA, two ribozymes, designated AT505 and AT589, were further analyzed. These two ribozymes were found to be effective after screening in PLC/PRF/5 cells transduced with retroviral vectors expressing these ribozymes (discussed below). For the construction of α1-AT ribozymes, AT505 and AT589, complementary oligonucleotides in which two restriction sites, BamHI and XbaI were introduced for further cloning, were added to the 5' end of the oligonucleotides. The sequences of oligonucleotides were as follows: sense primer AT505: 5'-tctagaTGTCCCCGAAGTTCTGATGAGTCCGCGAGG ACGA-3' (SEQ ID NO:2), antisense for AT505: 5'-ggatccAGAAGCCTTCACTGCTTTCGTCCTCGCGGA CTCAT-3' (SEQ ID NO:3), sense for AT589: 5'-tctagaTCAAGCTCCTTCTGATGAGTCCGCGAGGAC GAAAC-3' (SEQ ID NO:4), antisense for AT589: 5'-ggatccAAAATTGTGGATTTGGTTTCGTCCTCGCGG AC-3' (SEQ ID NO:5). The ribozymes were synthesized by incubating two oligonucleotides to form a hemiduplex, and PCR amplifications were performed. Then PCR products were directly cloned into pT7BIue-T vectors (Novagen) to generate plasmids, pT7AT505 and pT7AT589. Other ribozyme constructs, pT7AT204, pT7AT670, pT7AT777 and pT7AT918, were generated in the same manner. For the cloning of the α1-AT cDNA to generate the substrate RNA for AT505 and AT589 ribozyme in vitro cleavage reaction, two oligonucleotides were synthesized (sense primer: 5'-GATGAAATCCTGGAGGGC-3' (SEQ ID NO: 6), antisense primer: 5'-CCATTTGCCTTTAAAC-3'; (SEQ ID NO: 7)), and subjected to RT-PCR by using the RNA extracted from HepG2 cells, which are known to produce M type α1-AT. Davis, E. S. et al., (1990), *J. Biol. Chem.*, 265, 22153–22158. cDNA was synthesized using 1 μg of total RNA with reverse transcriptase (Promega, Madison, Wis.) and the antisense primer in a 20 μl volume containing final concentrations of 50 mM Tris-HCl (pH 8.3), 20 mM KCl, 10 mM MgCl$_2$, 5 mM dithiothreitol, and 1 mM of each deoxynucleotide triphosphate. Five microliters of the RT reaction was subjected to PCR amplification for 35 cycles consisting of 94° C. for 1.5 min, 50° C. for 1.5 min, and 72° C. for 2 min. The 365 base-pair PCR products were then cloned into the pGEM-T vector (Promega) to generate a plasmid, pGATS, which contains two GUC sites as the targets of α1-AT ribozymes, AT505 and AT589. The sequences of the ribozymes and α1-AT cDNA were confirmed by DNA sequencing using PRISM Ready Reaction DyeDeoxy Terminator Cycle Sequencing Kit (ABI).

Example 2
In Vitro Transcription and Ribozyme Cleavage Reaction

Plasmids T7AT505 and T7AT589, containing the ribozyme sequences, were digested with BamHI to linearize the plasmids, then transcribed with bacteriophage T7 RNA polymerase in the presence of [$\gamma$-$^{32}$p]UTP to generate AT505 and AT589 ribozymes of 118 and 124 bases, respectively. Plasmid pGATS, containing the $\alpha$1-AT mRNA sequence, was linearized with Sal I and transcribed with T7 RNA polymerase in the presence of [$\gamma$-$^{32}$p]UTP to generate substrate $\alpha$1-AT RNA of 440 bases. A 1:1 molar ratio of ribozyme RNA and substrate RNA was incubated in a 10 $\mu$l reaction volume containing 50 mM Tris-HCl (pH 7.5), 1 mM EDTA and 10 mM MgCL$_2$. These RNAs were heated to 95° C. for 2 min and cooled on ice. The reactions were performed at 37° C. for 30 to 60 min, then reactions were stopped by the addition of a equal volume of 95% formamide, 20 mM EDTA, 0.05% bromophenol blue, and 0.05% xylene cyanol, then heated to 65° C. for 5 min. The reaction products were separated on a 6% polyacrylamide-7 M urea gel in TBE buffer. The labeled RNAs were visualized by autoradiography.

Figure 2A:
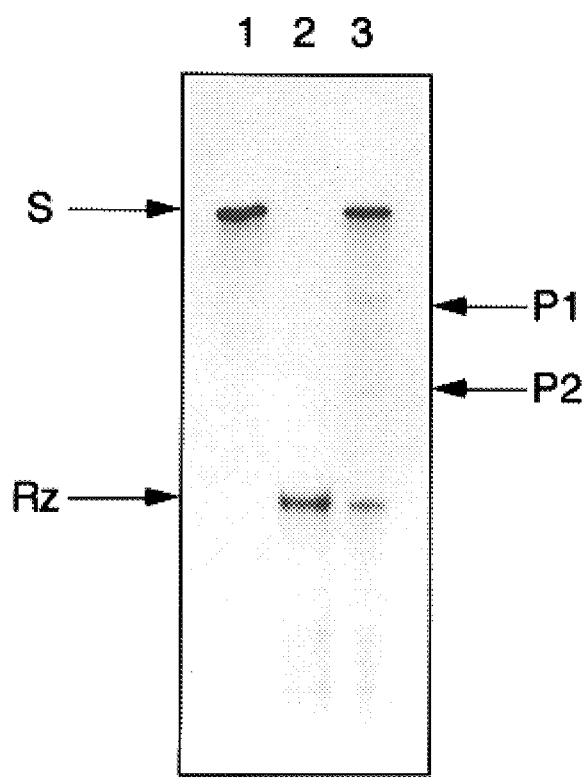
FIGS. 2A–2B are Northern blots of ribozyme cleavage products.
Figure 2B:
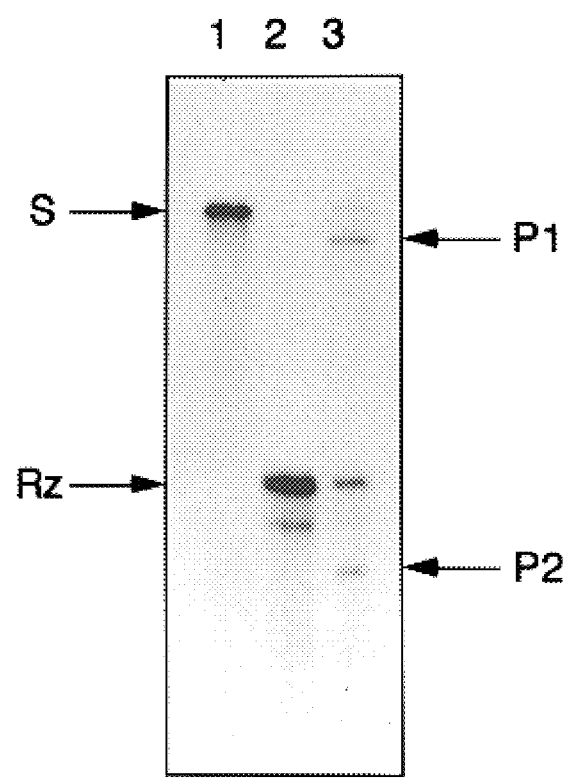

After 30 minutes the substrate $\alpha$1-AT RNA was cleaved at the expected specific sites, into 268 base (P1) and 172 base (P2) fragments by the AT505 ribozyme (FIG. 2A), and into 352 base (P1) and 88 base (P2) fragments by the AT589 ribozyme (FIG. 2B). Results showed that the AT589 ribozyme cleaved the substrate $\alpha$1-AT RNA at a higher efficiency, as compared to the AT505 ribozyme.

Example 3
Construction of Modified $\alpha$1-AT cDNA

Construction of a modified $\alpha$1-AT cDNA which would be resistant to an $\alpha$1-AT ribozyme and maintain normal function of the $\alpha$1-AT protein, but with altering the nucleotide sequences in the target region of AT589 ribozyme, is illustrated in FIG. 2A. As a template for modified $\alpha$1-AT cDNA, the full-length cDNA of $\alpha$1-AT was cloned into pT7Blue-T vector (Novagen) to generate pT7$\alpha$1AT by RT-PCR from the RNA of HepG2 hepatoma cells with two primers, AT-1 (sense): 5'-cgcatATGCCGTCTTCTGTCTCGTGG-3' (SEQ ID NO:8) and AT-2(antisense): 5'-ttagatctTTA TTTTTTGGGTGGGATTCAC-3' (SEQ ID NO:9). For the introduction of a mutation, two primers which contain modified nucleotide sequences of $\alpha$1-AT were synthesized. Sequences of oligonucleotide are as follows, and modified nucleotides are underlined: mAT-1(antisense): 5'-ATCTAGTTCTTTCACTAAGTCGACTATCTTCCC TTGAGTACCCTTCTCCAC-3' (SEQ ID NO:10) and mAT-2(sense): 5'-AAGATAGTCGACTTAGTGAAAGAACTAGAT AGAGACACATTTTTGCTCTG-3' (SEQ ID NO:11). First, two PCR fragments were amplified by using Vent DNA Polymerase (New England Biolab), one with AT-1 and ATm-1, and another one with ATm-2 and AT-2, respectively. These two PCR products were mixed and annealed, then an extension reaction was performed with Taq DNA polymerase(Perkin-Elmer, Branchburg, N.J.) at 72° C. for 10 min. This mixture was used for PCR amplification, as the template for the generation of modified $\alpha$1-AT with primers AT-1 and AT-2. The PCR products were cloned into pT7Blue-T vector(Novagen), to generate pT7m$\alpha$1AT.

Example 4
Retroviral Vectors

Two murine retroviral vectors, containing the neo gene as a selectable marker, were utilized for the expression of ribozymes in target cells. Retroviral vector, pSLXCMV, which contains an internal human intermediate early cytomegalovirus promoter was used for our initial works. Scharfmann, R. et al., (1991), *Proc. Natl. Acad. Sci. USA.*, 88, 4626–4630. For subcloning, the fragments of $\alpha$1-AT ribozymes were excised from plasmid pT7ATRzs with Bam HI, and cloned into the Bgl II site downstream of the internal CMV promoter in the pSLXCMV vector, to generate pSLX-CMVATRzs (FIG. 3A); pSLXCMVAT204, pSLXCMVAT505, pSLXCMVAT589, pSLXCMVAT670, pSLXCMVAT777 and pSLXCMVAT918. Retroviral vector pDCt2T (FIG. 3B) was used to insert $\alpha$1-AT ribozymes into the tRNA promoter cassette, tRNAiMet (D3-2) gene with a RNA polymerase III termination signal. Lee, S. W. et al., (1994), *J. Virol.*, 68, 8254–8264; Adeniyl-Jones, S. et al., (1984), *Nucl. Acid. Res.*, 12, 1101–1115. This construct is called a "double copy" vector because the tRNA gene is inserted in the U3 region of 3'-LTR, and when the recombinant virus is transduced into a target cell-line, the U3 region in 3'-LTR is used as a primer for synthesis of the 5'-LTR. Then, this tRNA promoter cassette is duplicated in the 5'-LTR. Briefly, for the ribozyme subcloning, the 70 bp fragments of $\alpha$1-AT ribozymes were excised from pT7ATRzs with Bam HI and cloned into the Bam HI site of pDCt2T to generate pDCt2ATRzTs; pDCt2AT204T, pDCt2AT505T, pDCt2AT589T, pDCt2AT670T, pDCt2AT777T and pDCt2AT918T. As a control for the ribozyme constructs, the abV$\kappa$ ribozyme was used. Duan, L., and Pomerantz, R. J., (1994), *Nucl. Acid. Res.*, 22, 5433–5438. The abV$\kappa$ ribozyme, which specifically targets mouse Ig gene kappa chain variable regions, was cloned into pSLXCMV or pDCt2T, to generate pSLXCMVabV$\kappa$r or pDCt2abV$\kappa$rT, respectively.

For construction of the bi-functional retroviral construct which carries both ribozyme and modified $\alpha$1-AT cDNA, modified $\alpha$1-AT cDNA was first cloned into pSLXCMV to generate pSLXCMVm$\alpha$1AT (FIG. 3C). The 1.3 kb fragment of human full-length, modified $\alpha$1-AT cDNA was excised from pT7malAT with Xba I and Sma I, and recloned into the Xba I-Pvu II site of the pSP72 vector (Promega) to generate pSP72m$\alpha$1AT. The modified $\alpha$1-AT cDNA then was cut with Bgl II and Xho I, and cloned into Bam HI-Bgl II site of pSLXCMV to generate pSLXCMVm$\alpha$1AT. Furthermore, to test the feasibility of ribozyme-mediated gene replacement by using a retroviral vector, a tRNA cassette containing the AT589 ribozyme and the CMV promoter-driven modified $\alpha$1-AT cDNA, which is engineered to be resistant to the attack from AT589 ribozyme, were placed into the same retroviral vector. For the construction of pSLXCMVm$\alpha$1AT-t2AT589T, the 600 bp fragment of the tRNA promoter cassette containing the AT589 ribozyme with a RNA polymerase III termination signal was excised from pDCt2AT589T with Bgl II and Mlu I, filled-in with Klenow enzyme, then cloned into the blunted Nhe I site located in the U3 region of the LTR of pSLXCMVm$\alpha$1AT to generate pSLXCMVm$\alpha$1AT-t2AT589T (FIG. 3D). Orientations and sequences of retroviral vectors were confirmed by DNA sequencing.

Example 5
Cells and Transfections

The human hepatoma-derived cell-line PLC/PRF/5 (ATCC CRL8024), HepG2 (ATCC HB 8065), human fibroblast cell AG1577 (34), and the retrovirus packaging cell-line PA317 (ATCC CRL 9078); *Mol. Cell. Biol.*, 6, 2895–2902 (1986); were grown in DMEM medium supplemented with 10% fetal bovine serum. Subconfluent PA317 cells were transfected with 5 $\mu$g of plasmids pSLXCMVATRzs, pDCt2ATRzs, pSLXCMVabV$\kappa$r, pDCt2abV$\kappa$rT, pSLXCMVm$\alpha$1AT, or pSLXCMVm$\alpha$1ATt2AT589T by lipofectin, according to the manufacture's instructions (Gibco-BRL, Gaithersburg, Md.). After 48 hours, medium containing recombinant retrovirus particles was collected, and PLC/PRF/5 cells were infected with the recombinant virus for 48 hours in the presence of 8 µg/ml polybrene. Then, PLC/PRF/5 cells were selected with 1 µg/ml of G418 (Gibco-BRL) for 3 weeks. G418-resistant clones were isolated under microscopy or pooled. Both individual clones and mixed pooled population of PLC/PRF/5 cells were subjected to further analysis.

Example 6
RNA Analysis

Total RNA from PLC/PRF/5 cells, transduced or non-transduced with retroviruses, was extracted by a modification of the method of Chomczynski and Sacchi. Chomczynski, P. and Sacchi, (1987), Anal. Biochem., 162, 156–159. Expression of mRNAs was detected by Northern blot hybridization analysis, as previously described; Frizell, E. et al., (1995), Hepatology, 21, 847–854; employing a human α1-AT cDNA probe, α1-AT ribozyme cDNA probe, and a GAPDH cDNA as a control. Yun-Tso, J. et al., (1985), Nucl. Acid. Res., 13, 2485–2502. Samples of total RNA (20 µg) were denatured in buffer containing 0.5 mg/L glyoxal, 50% dimethyl sulfoxide, 10 mM phosphate, electrophoresed in 1% agarose gels, transferred to a GeneScreen filter (New England Nuclear, Boston, Mass.), and baked for 2 hours at 80° C. The filters were hybridized and were subsequently hybridized under stringent conditions with cDNA labeled with [$\alpha$-$^{32}$P] dCTP by a primer extension kit (Amersham, Arlington Heights, Ill.). After hybridization, the filters were washed and the signals were visualized by autoradiography.

Example 7
Protein Extraction and Western Blot Analysis

PLC/PRF/5 cells, transduced with retroviruses or non-transduced, were plated in a 12-well culture dishes at a density of 5×10$^5$ cells/well and lysed as previously described. Frizell, E. et al., (1995), Hepatology, 21, 847–854. Proteins were subjected to electrophoresis in 10% sodium dodecyl sulfate polyacrylamide gels and subsequently transferred to a Poly Screen (PVDF) membrane (DuPont Inc). After the membrane was blocked in 5% non-fat dry milk, the specific protein expression was detected with either rabbit polyclonal anti-human α1-AT antibodies (Boehringer Mannheim, Indianapolis, Ind.) or rabbit anti-human b-actin antibodies (Sigma, St. Louis, Mo.), using the DuPont western Blot Chemiluminescence kit with manufacture suggested protocol (DuPont Inc.)

Figure 4:
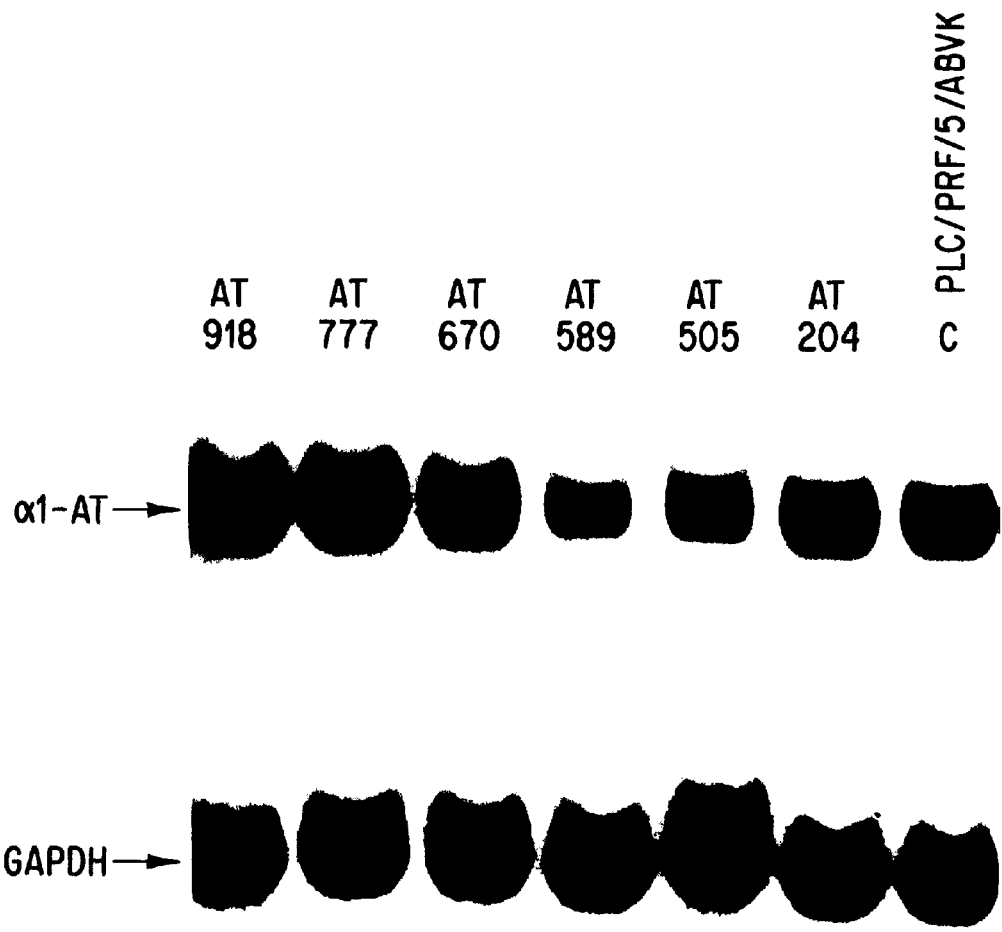
FIG. 4 is a Northern blots of α1-AT mRNA and GAPDH mRNA in the PLC/PRF/5 mixed population cells transduced with retroviral vectors carrying ribozymes under the control of tRNA promoter.
Figure 5A:
FIGS. 5A and 5B are Northern blots of α1-AT/GAPDH mRNAs in the PLC/PRF/5 cloned population cells transduced with retroviral vectors which carry ribozymes under the control of tRNA promoter.
Figure 5B:
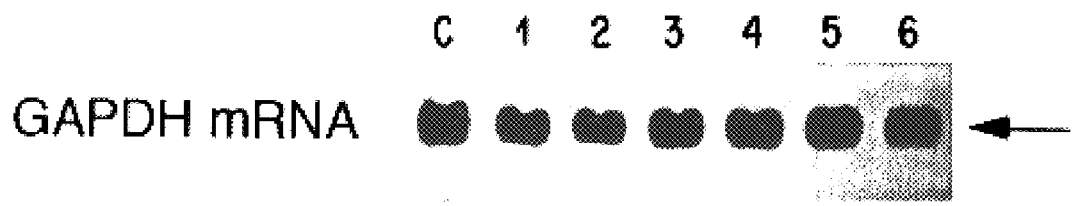
Figure 5C:
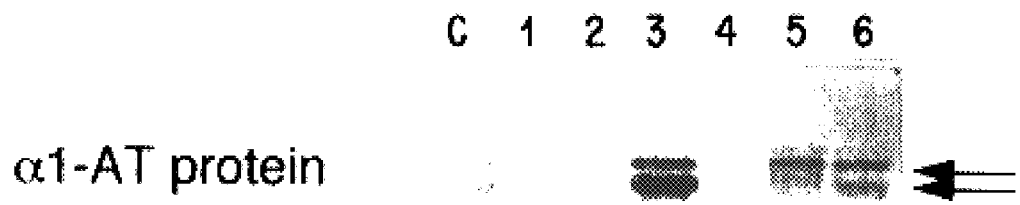
FIGS. 5C and 5D are western blots of α1-AT b-actin proteins in the PLC/PRF/5 cloned population cells transduced with retroviral vectors which carry ribozymes under the control of tRNA promoter.
Figure 5D:
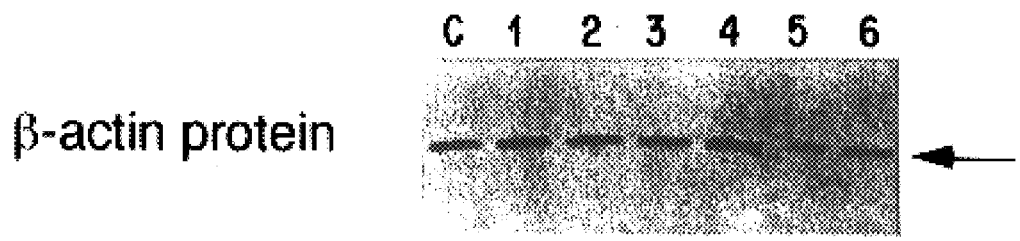

Example 8
Inhibition of α1-AT mRNA in PLC/PRF/5 Cells Transduced with Retroviral Vectors Expressing Ribozymes To study the effect of ribozymes on the expression of α1-AT in a human hepatoma-derived cell-line, we transduced PLC/PRF/5 cells which actively produce α1-AT with the pLXSCMV retroviral vector containing a panel of human α1-AT ribozymes and control ribozymes as described in Example 5. After G418 selection for 3 weeks, G418-resistant clones were isolated, then both pooled mixed populations and individual resistant clones were analyzed for α1-AT expression. Northern blot analysis of RNA extracted from PLC/PRF/5 cells transduced with α1-AT ribozymes, which were driven by the internal CMV promoter which uses RNA II polymerase for transcription, revealed that none of these cells showed a reduction of α1-AT mRNA expression, even in single cell clones. This occurred despite the fact that expression of α1-AT ribozymes was detected more than two months after G418 selection. Considering the large size of CMV driven RNA and its complex structure, this moiety may not be able to efficiently target α1-AT mRNA. We further tested all ribozymes which were expressed from the tRNA transcription unit. Of the PLC/PRF/5 cells, transduced with α1-AT ribozymes expressed from the human tRNA promoter cassette transcribed by RNA—polymerase III, only the cells transduced with AT505 and AT589 showed significant reduction of α1-AT mRNA in the pooled populations (FIG. 4). Therefore, further detailed parameters were analyzed in the cells transduced with either AT505 or AT589, employing the tRNA promoter. The levels of α1-AT mRNA expression in the cells transduced with AT505 ribozyme or AT589 ribozyme were reduced to 47% and 31% of the levels of non-transduced PLC/PRF/5 cells, respectively, by densitometric scanning, and the reduced α1-AT mRNA expression in these cells was maintained more than three months. This different efficiency in the decrease of α1-AT mRNA expression between AT505 and AT589 corresponds to the difference of cleavage efficiency between AT505 and AT589 in the cell-free system. The PLC/PRF/5 cells transduced with a control ribozyme abVk showed no reduction of α1-AT mRNA expression, compared with non-transduced PLC/PRF/5 cells (FIG. 4). Moreover, there was no change in expression of a house-keeping gene, GAPDH, in the cells transduced with all of the ribozymes (FIG. 4). These data suggest that α1-AT ribozymes transcribed by RNA polymerase III can specifically inhibit endogenous α1-AT mRNA expression in PLC/PRF/5 cells. Of the individual clones transduced with the AT589 ribozyme, driven by tRNA promoter, half showed reduction in α1-AT mRNA and protein levels, although there was variation between individual clones (FIG. 5). Some clones showed more than 90% reduction of α1-AT mRNA and protein levels compared to the non-transduced controls, whereas GAPDH mRNA and b-actin protein levels did not demonstrate any significant changes among these clones (FIG. 5). In the Northern blots, low molecular weight species of α1-AT mRNA cleaved by ribozymes could not be detected, probably due to rapid degradation of the cleaved RNA.

Figure 3:
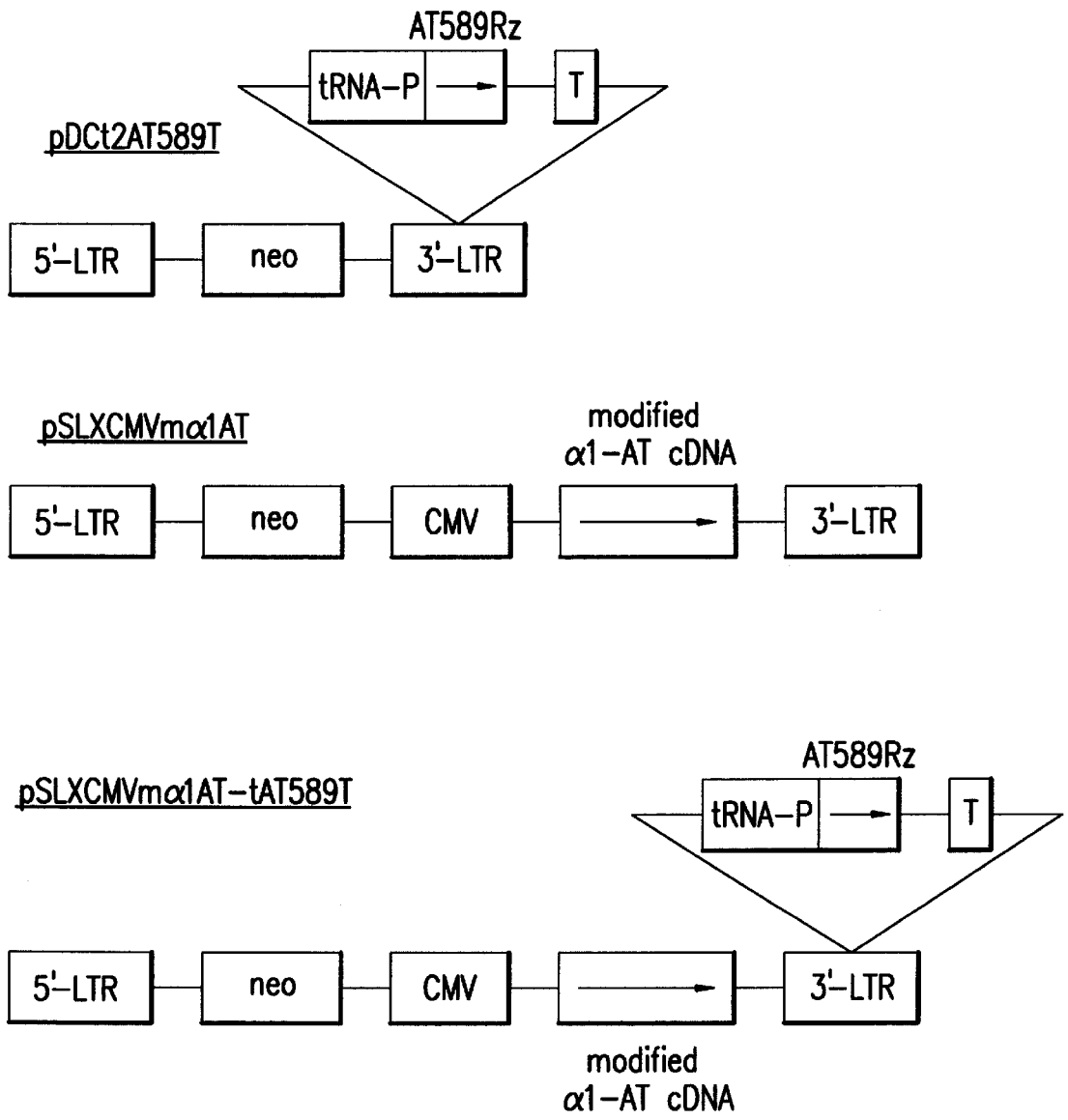
FIG. 3 is a schematic representation of retroviral vectors. From the internal CMV promoter pSLXCMVATRzs (A); (here, pSLXCMVAT589Rz is representative.) (B): the tRNA promoter cassette with RNA polymerase III termination signal (T) pDCt2ATRzs (pDCt2AT589T as example.) (C) Retroviral vector which expresses the modified α1AT cDNA from CMV promoter (pSLXCMVmα1AT). (D) Bi-functional retroviral vector which expresses CMV promoter-driving modified α1-AT and tRNA-driving AT589 ribozyme (pSLXCMVmα1AT-t2AT589T).

Example 9
Ribozyme Mediated Replacement of Endogenous α1-AT Expression with Modified Wild-type α1-AT Among the α1-AT ribozymes tested in retrovirally transduced PLC/PRF/5 cells, AT589 showed the most efficient inhibition of α1-AT mRNA expression. To compensate for the endogenous α1-AT expression reduced by the AT589 ribozyme, we modified the nucleotide sequences of the target site of AT589 in the full-length α1-AT cDNA, without changing amino acid sequences, to create the modified α1-AT cDNA that would be resistant to AT589 ribozyme cleavage (FIG. 6). To achieve the reduction of endogenous α1-AT and replacement with modified α1-AT simultaneously, modified α1-AT cDNA was constructed under the control of the CMV promoter and the tRNA promoter-driven AT589 ribozyme cassette was placed in the same retroviral vector to generate pSLXCMVmα1AT-tAT589T (FIG. 3). The PLC/PRF/5 cells were transduced with this bi-functional vector, and the expression of endogenous α1-AT and modified α1-AT was detected simultaneously by Northern blot according to the different sizes of both transcripts. The transcripts size of modified α1-AT is expected to be 1 kb longer than that of the endogenous mRNA, because there are tRNA promoter cassette and retroviral sequences between the stop codon of α1-AT cDNA and the polyadenylation signal of the 3'LTR. The Northern blot analyses demonstrated the effective reduction of endogenous α1-AT mRNA and the expression of modified α1-AT in the mixed populations of transduced PLC/PRF/5 cells (FIG. 7). Hybridization with the AT589 ribozyme probe showed the two transcripts which corresponded to the transcripts from the CMV promoter and from the tRNA promoter, were equally well expressed (FIG. 8). These data demonstrate that it is possible to replace endogenous α1-AT gene expression with modified α1-AT, by a ribozyme-mediated approach.

Example 10

Introduction

The liver disease of α1AT deficiency is generally though to be caused by the accumulation of an abnormal α1AT protein in hepatocytes, whereas the lung disease is thought to be due to a relative lack of the normal protein in the circulation. Therefore, the present invention provides an approach to prevent and treat α1AT disease to both inhibit the expression of the mutated α1AT gene, and to provide a means of synthesizing the normal protein. To do this, specific hammerhead ribozymes were designed that are capable of cleaving the α1AT mRNA at specific sites. A modified α1AT cDNA was constructed to endcode the protein while having sequence modifications that render it not susceptible to ribozyme cleavage. One ribozyme was effective in inhibiting α1AT cDNA not susceptible to ribozyme cleavage. One ribozyme was effective in inhibiting α1AT expression in a human hepatoma cell line using either a retroviral or simian virus (SV40) vector system; moreover, the newly developed SV40 vector was somewhat better in that it worked with either a polymerase II or polymerase III promoter, and in unselected cells. In addition, the hepatoma cell line was stably transduced with a modified α1AT cDNA that was capable of producing wild-type α1AT protein, but was not cleaved by the ribozyme that decreased endogenous α1AT expression. These results demonstrate that ribozymes may be employed for the specific inhibition for an abnormal α1AT gene product, the first step in designing a gene therapy for the disease.

Although several studies have focused on the delivery of the normal α1AT gene into hepatocytes or airway cells to restore normal α1AT production and to protect lung tissue, these approaches do not affect the liver disease. It would appear that the best way to treat α1AT deficiency disease is to reduce the production of the endogenous mutant form of α1AT protein and to increase the synthesis of the normal protein. The reduction of α1AT expression can be achieved by several strategies, such as antisense, gene specific ribozymes, α1AT transcription factor specific-inhibitors, or intracellular expression of antibody to the mutant from of the α1AT protein. By using a hammerhead ribozyme, the mutant form of α1AT mRNA was targeted by using α1AT guide sequences attached to the ribozyme catalytic core sequence. Furthermore, the corresponding cloned wild-type α1AT cDNA GUC and guide region nucleotide sequences was changed while maintaining the amino acid sequence. This modified "wild-type" α1AT mRNA is resistant to the ribozyme.

A simian virus (SV)40 transfer vector system described in PCT/US95/17065, which is incorporated herein by reference, was used. This system both delivers the gene of interest to the target organ and allows for its adequate expression. The transduction of an effective α1AT ribozyme in this SV40 vector system inhibited the expression of the α1AT gene in a human hepatoma-derived cell line. At the same time, the modified α1AT cDNA that was constructed and that is capable of producing the normal α1AT protein while its RNA is resistant to ribozyme cleavage was also delivered using the system.

MATERIALS AND METHODS

Ribozyme Design and Cloning

The ribozymes that target α1AT mRNA at 204 and 589 were selected for testing in the SV40-derived system. Each ribozyme is denoted by the nucleotide position of the first G of the target GUC triplet when the first A of the initiation codon AUG is numbered as 1. For the design of the ribozymes, 11 to 15 bases of antisense sequence against α1AT mRNA were flanked on both sides of the hammerhead motif to allow the ribozyme to associate with α1AT mRNA through their complementary sequences. For the construction of the ribozymes, two complementary oligonucleotides were synthesized on the DNA synthesizer Model 392 (Applied Biosystems, Inc., Foster City, Calif.). The ribozymes were synthesized by incubating two oligonucleotides to form a hemiduplex, and PCR amplifications were performed. Then the PCR products were cloned directly into the PT7Blue-T vector (Novagen, Madison, Wis.) to generate plasmids PT7ATRzs, which contained each ribozyme under the control of the bacteriophage T7 promoter.

Modified α1AT cDNA: according to the design of the modified α1AT cDNA which is resistant to the AT589 ribozyme and yet codes for a normal α1AT protein, the modified cDNA has the third nucleotide mutated in the 589 region (GTC→GTG), and n the immediate 5' and 3' flanking region. The full-length α1AT cDNA was cloned into pT7Blue-T vector (Novagen) to generate PT7 α1AT by RT-PCR, employing RNA from Hep G2 cells. Then modified oligonucleotides were used as templates for the PCR reaction leading to he generation of the modified α1AT. The PCR products were then cloned into the pT7Blue-T vector, to generate PT7m α1AT.

Retroviral vectors: The retroviral vectors, containing the neo gene as a selectable marker, were utilized for the expression of ribozymes in cells. One was constructed from PSLXCMV (Scharfmann, R. et al. 1991 Proc. Natl. Acad. Sci. USA 88:4626–4630, which is incorporated herein by reference) which contains the human intermediate early cytomegalovirus (CMV) promoter. For the subcloning, the fragment of the α1AT ribozyme was excised from plasmid pT7AT589, and cloned into the BglII site downstream of the CMV promoter in the pSLXCMV vector to generate pSLX-CMVAT589 (FIG. 9A). Retroviral vector pDCt2T (Lee, S. W. et al. 1994 J. Virol. 68:8254–8264, which is incorporated herein by reference) which is called a "double copy" vector (FIG. 9B), was used to insert α1AT ribozymes into the tRNA promoter cassette, including the tRNAiMet (Δ3-2) gene with an RNA polymerase III termination signal. For the subcloning, the fragments of α1AT ribozymes were excised from pDCt2ATRzTs. After subcloning, the modified α1AT cDNA was cut with BglII and XhoI, and cloned into the BamHI-BglII site of pSLXCMV to generate pSLXCMVM α1AT (FIG. 9C). Orientations and sequences of the vectors were confirmed by DNA sequence analysis.

Cells and Transfection

The human hepatoma-derived cell line PLC/PRF/5 and the retrovirus packaging cell line PA317 were grown in DMEM supplemented with 10% fetal bovine serum. Subconfluent PA 317 cells were transfected with plasmid pSLX-CMVATRzs. PSLXCMVα1AT or pDCt2ATRzTs by lipofectin (Gibco BRL, Gaithersburg, Md.) according to the manufacturer's instruction manual. After 48 hours, medium containing recombinant retrovirus particles was collected, and PLC/PRF/5 cells were transduced with the recombinant virus for 48 hours; then PLC/PRF/5 cells were selected with 1 mg/ml of G418 (Gibco BRL) for 3 weeks. G418 resistant clones were picked under microscopy and subjected to further analysis.

Construction of SV40 Derivative Viruses for Transduction

The details of the construction and application of modified SV40 vectors for the purpose of gene transduction are reported in Strayer, D. S. 1996 J. Biol. Chem. 27:24741–24746 and Strayer, D. S. and J. Milano 1996 Gene Therapy 3:581–587, which are both incorporated herein by reference). The 5.24 kb SV40 genome was cloned as a BamHI fragment into pBR322. The viral genome was modified by excising the gene for large T antigen (Tag) as an AvrII-BclI fragment, and replacing it by a modified pGEM7 polylinker, whose Sp6 and T7 promoters were flanked by AvrII and BclI restriction sites, respectively. This procedure also excises the genes for the small T antigen, but leaves the SV40 early promoter and the SV40 polyadenylation signal intact. The late viral genes, VP1, VP2, and VP3, which encode capsid proteins, are also undisturbed in this construct. This modified SV40 genome, still in pBR322, was named pBSV (ΔT').

To produce virus from this construct, the viral genome was excised from pBR322, gel purified, and recircularized. It was then transfected into COS-7 cells (ATCC) for packaging. The COS-7 cells used for this procedure contain a copy of the SV40 genome that is deficient in that it has a deletion in the origin of replication. Thus, these cells supply the missing Tag in trans, and permit the replication and packaging of the resultant Tag-deleted viruses. TC7 cells lacking the viral genome do not permit replication of Tag-deleted SV40 derivatives. This system therefore does not depend upon the presence of helper virus, but relies on expression of Tag by the packaging cells.

After visual examination for virus-induced cytopathic effect showed that >50% of COS-7 cells have been infected with virus, virus was released from the cells by freezing and thawing, followed by sonication. Most of the infectious virus remained associated with the cell cytoskeleton. Virus was titered by measuring the concentration of infectious units that can penetrate target cells by an in situ polymerase chain reaction. In general, yields of infectious virus without further purification are $10^9$ TCID$_{50}$/ml.

Concentration of virus to ~$10^{10}$ TCID$_{50}$ml was accomplished by discontinuous sucrose density ultracentrifugation. Culture medium containing the SV40 derivative viruses was mixed 1:10 with a solution of 10% Triton X-100+5% deoxycholate, and layered onto a discontinuous sucrose density gradient (20% sucrose/75% sucrose) and centrifuged at 22,500 rpm in an SW28 rotor in a Beckman ultracentrifuge. This procedure dissociates virus from the associated COS cell cytoskeleton. Virus concentrated at the interface between the two sucrose layers is recovered, then dialyzed vs. normal saline to remove excess sucrose. These preparations are titered prior to use.

The ribozyme constructs described above were cloned into the multiple cloning site of pBSV(ΔT'). These cloning procedures yielded two different types of ribozyme-containing plasmids: one in which ribozyme expression was driven by the SV40 early promoter, and another in which the tRNA promoter was used to drive ribozyme transcription (FIG. 10). Replication-incompetent SV40 derivative viruses containing these ribozyme constructs were produced and titered as described above.

Recombinant viruses, containing the ribozymes under the control of either the tRNA or SV40 early promoter, were used to transduce PLC/PRF/5 cells at an moi of either 10 or 100. In one experiment, the hepatoma cells were stably transduced with the modified α1AT cDNA, by the use of vector pSLXCMVmα1AT prior to transduction with the SV40-derived vectors. Two days following the transduction, RNA was isolated from an unselected population of cells and evaluated by Northern blot hybridization analysis.

RNA Analysis

Total RNA from PLC/PRF/5 cells transduced or non-transduced with viral constructs was extracted. Messenger RNA's were detected by Northern hybridization analysis employing a human α1AT cDNA probe; human fibronectin, human transferrin and glyceraldehyde dehydrogenase (GAPDH) were employed as controls. Samples of 20 μg of total RNA were denatured in buffer containing 0.5 mg/L glyoxal, 50% dimethyl sulfoxide, 10 mM phosphate, electrophoresed in 1% agarose gel, transferred to a GeneScreen filter (New England Nuclear, Boston, Mass.), and baked for 2 hours at 80° C. The filters were prehybridized and were subsequently hybridized under stringent conditions with cDNA's labeled with [a-$^2$P] dCTP by a primer extension kit (Amersham, Arlington Heights, Ill.). After hybridization, the filters were washed and the signals were visualized by autoradiography.

RESULTS

To study the effects of ribozymes on the expression of α1AT in a human hepatoma-derived cell line, we transduced PLC/PRF/5 cells that actively produce α1AT with either retroviral or SV40 recombinant viruses. Both polymerase II and III promoters were employed to drive expression of the ribozymes.

In one series of studies, retroviral vectors were used to transfer ribozymes. RNA was extracted from a pooled population of cells that had been transduced with the retroviral vectors and selected with G418 for three weeks. Representative Northern blot hybridization analysis of ribozyme AT589 (FIG. 11) indicated that whereas ribozyme expression driven by a tRNA promoter decreased α1AT mRNA expression, no such effect on α1AT mRNA expression was found when the CMV promoter was used to drive ribozyme expression. Hybridization with GAPDH and transferrin indicated that approximately equal amounts of RNA were applied per lane. In cells transduced with a control ribozyme construct, no change in α1AT expression occurred. Six ribozymes for α1AT were tested and the three active ribozymes showed the same result: a tRNA promoter was necessary for successful ribozyme effect when the retroviral vector was employed.

The SV40 vector system was somewhat more effective. PLC/PRF/5 cells were transduced using three different SV40 constructs, each containing either AT204 or 589 ribozyme. One construct employed the AT204 ribozyme driven by the tRNA promoter, one used the AT589 ribozyme under the control of the SV40 early promoter, and the third used the 589 ribozyme with the tRNA promoter. No selection was applied to these cells. Forty eight hours following transduction, RNA was isolated from the unselected populations of cells and assayed by Northern blot hybridization analysis. α1AT mRNA levels were significantly decreased in cells infected with the recombinant viruses in which ribozyme expression were driven by either the SV40 early promoter or the tRNA promoter, whereas there was no difference in GAPDH expression (FIG. 12).

Further studies were done with ribozyme AT589 constructs because they generated consistently high ribozyme activity. FIG. 13 is a series of representative Northern blots of RNA isolated from an unselected population of cells 48 hours following transduction with a control construct, SVCAT, or with vector constructs containing 589AT ribozymes. The blots demonstrate the effectiveness of the ribozymes and their selective and specific properties.

To compensate for the endogenous α1AT expression being reduced by the AT589 ribozyme, the nucleotide sequences of the target site of AT589 in the full-length α1AT cDNA was modified, without changing amino acid sequences, to create the modified α1AT cDNA that would be resistant to AT589 ribozyme cleavage. To test the effectiveness of this construct, the PLC/PRF/5 cell line were stably transfected with the modified α1AT cDNA construct in a retroviral vector under the control of the CMV promoter. When this line was then transduced with the SV40 vectors containing ribozymes, the endogenous α1AT mRNA expression was considerably decreased by the two AT589 ribozyme constructs. The 204 construct had little if any effect. There was no effect of the ribozymes on the modified α1AT mRNA (FIG. 14A). Transduction with a control construct, SV(Δ)CAT, had no effect on the expression of either the endogenous or exogenous α1AT mRNA levels. The specific nature of the ribozymes was demonstrated again when GAPDH was employed as a control; no effect on GAPDH expression was found with any ribozyme. Densitometry scanning of the experiments confirmed that the 589AT ribozymes were effective in selectively affecting the endogenous α1AT, without having an effect on the modified species (FIG. 14B).

Densitometry scanning of three sets of experiments indicated that the SVP.AT589 construct (driven by the SV40 early promoter) decreased α1AT expression by 70.8±4.0% (mean±S.E.M.). The SV(Δ)tAT589 construct (driven by the tRNA promoter) decreased α1AT expression by 74.8±2.1%.

DISCUSSION

The data demonstrate that hammerhead ribozymes may be effectively used to inhibit expression of α1AT in a hepatoma-derived cell line. The inhibitory activity of the ribozymes seems to depend on the ability to provide a high level of ribozyme expression. The data demonstrate that the ribozymes were effective whether they were transduced using the standard retroviral vector system employing a selected population of stably transfected cells, or employing the novel SV40 vector system without selecting for transduced cells. In addition, the results show that it is possible to transduce a modified cDNA into hepatoma cells, and that the transcript which encodes for the wild-type α1AT protein is not susceptible to ribozyme cleavage. These results model the use of a "bifunctional" vector for the prevention and treatment of α1AT deficiency.

Our data indicated that a tRNA promoter produced adequate expression of the ribozyme when the retroviral vector was employed; the data using the CMV promoter did not adequately express the ocnstruct. The tRNA promoter is probably the best promoter for transcribing short RNA species. Modifications of the 3'-end of ribozymes have been reported to dramatically affect the intracellular stability and cleavage efficiency. The RNAs transcribed by RNA polymerase II have long poly (A) tails which may affect the structure of the ribozyme and subsequently disturb the effective association with target RNA and the cleavage reaction. In addition, retroviral transcripts are often generated from long terminal repeat (LTR) to LTR, providing very bulky flanking RNA sequences that may interfere with catalytic and/or binding activation.

It appears that the SV40 vector system may be more efficient in transducing and expressing its transgene than the retroviral system. α1AT expression was inhibited using recombinant SV40 employing either the SV40 early promoter or the tRNA promoter. The effect on α1AT expression occurred in an unselected population of cells. This contrasts with the experience with the retroviral system, where cells were selected by G418 resistance, and only successfully transduced cells were evaluated. Such selection was not used in the SV40 experiments; RNA was isolated from the entire population of cells 48 hours post-infection with recombinant SV40 vector. No attempt was made to select a subpopulation of transduced cells.

Employing two different vector systems, we have demonstrated the first steps in the inhibition of abnormal α1AT gene expression, as well as the synthesis of a normal gene product for the treatment of α1AT deficiency disease.

What is claimed is:

1. A bifunctional expression vector for replacement of a mutant gene, said vector comprising a regulatory cassette encoding a site-specific hammerhead ribozyme which degrades the mRNA of said mutant gene at a GUX triplet site within a defined region of the mRNA, wherein X is selected from the group consisting of C, U, and A, said defined region comprising said GUX triplet site and two flanking regions flanking said GUX triplet site, said hammerhead ribozyme comprising a structural domain interposed between two complementarity regions which are complementary to said two flanking regions, wherein each of said two complementarity regions has a length of at least 10 nucleotide residues, and wherein the combined nucleotide sequence of said structural domain and said two complementarity regions is selected from the group consisting of SEQ ID NOs: 13, 15, 17, 19, 21, and 23; and a structural cassette comprising a normal copy of said mutant gene, wherein the nucleotide sequence of said defined region of the mRNA of said normal copy differs from the nucleotide sequence of said defined region of the mRNA of said mutant gene, whereby said hammerhead ribozyme does not degrade the mRNA of said normal copy.

2. The bifunctional expression vector of claim 1, wherein the combined nucleotide sequence of said structural domain and said two complementarity regions is SEQ ID NO: 17.

3. A bifunctional expression vector for replacement of a mutant gene, said vector comprising a regulatory cassette encoding ribozyme AT589; and a structural cassette comprising a gene encoding α1AT, wherein the portion of said gene which normally has the sequence SEQ ID NO: 25 is altered such that it has the sequence SEQ ID NO: 26.

4. A bifunctional expression vector for replacement of a mutant gene, said vector comprising a regulatory cassette encoding a site-specific hammerhead ribozyme which degrades the mRNA of said mutant gene at a GUX triplet site within a defined region of the mRNA, wherein X is selected from the group consisting of C, U, and A, said defined region comprising said GUX triplet site and two flanking regions flanking said GUX triplet site, said hammerhead ribozyme comprising a structural domain interposed between two complementarity regions which are complementary to said two flanking regions, wherein each of said two complementarity regions has a length of at least 10 nucleotide residues, and wherein said structural domain has the sequence SEQ ID NO: 1; and a structural cassette comprising a normal copy of a gene encoding α1AT, said gene having at least one modification selected from the group consisting of (a) substitution of a guanine residue in place of the adenine residue at position 576 of the wild type α1AT gene;

(b) substitution of an adenine residue in place of the thymine residue at position 579 of the wild type α1AT gene;

(c) substitution of a cytosine residue in place of the guanine residue at position 582 of the wild type α1AT gene;

(d) substitution of a cytosine residue in place of the thymine residue at position 585 of the wild type α1AT gene;

(e) substitution of an adenine residue in place of the guanine residue at position 588 of the wild type α1AT gene;

(f) substitution of a guanine residue in place of the cytosine residue at position 591 of the wild type α1AT gene;

(g) substitution of an adenine residue in place of the guanine residue at position 594 of the wild type α1AT gene;

(h) substitution of an adenine residue in place of the guanine residue at position 597 of the wild type α1AT gene;

(i) substitution of an adenine residue in place of the thymine residue at position 600 of the wild type α1AT gene; and (j) substitution of an adenine residue in place of the cytosine residue at position 603 of the wild type α1AT gene, whereby said hammerhead ribozyme does not degrade the mRNA of said normal copy.

\* \* \* \* \*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: RNA (genomic)

(ix) FEATURE:
      (A) NAME/KEY: stem_loop
      (B) LOCATION: 8..19

(xi) SEQUENCE DESCRIPTION: SEQ ID NO:1:

CUGAUGAGUC CGCGAGGACG AAAC                        24

(2) INFORMATION FOR SEQ ID NO:2:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

TCTAGATGTC CCCGAAGTTC TGATGAGTCC GCGAGGACGA        40

(2) INFORMATION FOR SEQ ID NO:3:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GGATCCAGAA GCCTTCACTG CTTTCGTCCT CGCGGACTCA T        41

(2) INFORMATION FOR SEQ ID NO:4:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TCTAGATCAA GCTCCTTCTG ATGAGTCCGC GAGGACGAAA C        41

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGATCCAAAA TTGTGGATTT GGTTTCGTCC TCGCGGAC        38

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATGAAATCC TGGAGGGC        18

(2) INFORMATION FOR SEQ ID NO:7:

(i) SEQUENCE CHARACTERISTICS:

(A) LENGTH: 16 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:7:

CCATTTGCCT TTAAAC                                                    16

(2) INFORMATION FOR SEQ ID NO:8:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:8:

CGCATATGCC GTCTTCTGTC TCGTGG                                         26

(2) INFORMATION FOR SEQ ID NO:9:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:9:

TTAGATCTTT ATTTTTTGGG TGGGATTCAC                                     30

(2) INFORMATION FOR SEQ ID NO:10:

(i) SEQUENCE CHARACTERISTICS:
       (A) LENGTH: 51 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:10:

ATCTAGTTCT TTCACTAAGT CGACTATCTT CCCTTGAGTA CCCTTCTCCA C             51

(2) INFORMATION FOR SEQ ID NO:11:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:11:

AAGATAGTCG ACTTAGTGAA AGAACTAGAT AGAGACACAT TTTTGCTCTG               50

(2) INFORMATION FOR SEQ ID NO:12:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: mRNA (xi) SEQUENCE DESCRIPTION: SEQ ID NO:12:

AGCUGGCACA CCAGUCCAAC AGCACCAAUA                                     30

(2) INFORMATION FOR SEQ ID NO:13:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: RNA (genomic)

(ix) FEATURE:
            (A) NAME/KEY: stem_loop
            (B) LOCATION: 22..33

(xi) SEQUENCE DESCRIPTION: SEQ ID NO:13:

UAUUGGUGCU GUUGCUGAUG AGUCCGCGAG GACGAAACUG GUGUGCCAGC U             51

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:14:

AGAAGCCUUC ACUGUCAAGG AGCUUGA                                        27

(2) INFORMATION FOR SEQ ID NO:15:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: RNA (genomic)

(ix) FEATURE:
            (A) NAME/KEY: stem_loop
            (B) LOCATION: 19..30

(xi) SEQUENCE DESCRIPTION: SEQ ID NO:15:

UCUUGCUCCU UCUGAUGAGU CCGCGAGGAC GAAACAGUGA AGGCUUCU                 48

(2) INFORMATION FOR SEQ ID NO:16:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:16:

AAUUGUGGAU UUGGUCAAGA GCUUGA                                         26

(2) INFORMATION FOR SEQ ID NO:17:

(i) SEQUENCE CHARACTERISTICS:

(A) LENGTH: 47 base pairs
            (B) TYPE: nucleic acid
            (C) STRANDEDNESS: single
            (D) TOPOLOGY: linear (ii) MOLECULE TYPE: RNA (genomic)

(ix) FEATURE:
            (A) NAME/KEY: stem_loop
            (B) LOCATION: 18..29

(xi) SEQUENCE DESCRIPTION: SEQ ID NO:17:

UCAAGCUCUU CUGAUGAGUC CGCGAGGACG AAACCAAAUC CACAAUU        47

(2) INFORMATION FOR SEQ ID NO:18:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:18:

GAGACCCUUU GAAGUCAAGG ACACCGA        27

(2) INFORMATION FOR SEQ ID NO:19:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: RNA (genomic)

(ix) FEATURE:
            (A) NAME/KEY: stem_loop
            (B) LOCATION: 19..30

(xi) SEQUENCE DESCRIPTION: SEQ ID NO:19:

UCGGUGUCCU UCUGAUGAGU CCGCGAGGAC GAAACUUCAA AGGGUCUC        48

(2) INFORMATION FOR SEQ ID NO:20:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:20:

ACUGUAAGAA GCUGUCCAGC UGGGUGCUGC        30

(2) INFORMATION FOR SEQ ID NO:21:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: RNA (genomic)

(ix) FEATURE:
            (A) NAME/KEY: stem_loop
            (B) LOCATION: 22..33

(xi) SEQUENCE DESCRIPTION: SEQ ID NO:21:

GCAGCACCCA GCUGCUGAUG AGUCCGCGAG GACGAAACAG CUUCUUACAG U            51

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:22:

AUGAAGACAG AAGGUCUGCC AGCUUACAU                                    29

(2) INFORMATION FOR SEQ ID NO:23:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (genomic)

(ix) FEATURE:
        (A) NAME/KEY: stem_loop
        (B) LOCATION: 21..32

(xi) SEQUENCE DESCRIPTION: SEQ ID NO:23:

AUGUAAGCUG GCACUGAUGA GUCCGCGAGG ACGAAACCUU CUGUCUUCAU             50

(2) INFORMATION FOR SEQ ID NO:24:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

Lys Ile Val Asp Leu Val Lys Glu Leu Asp
1               5                  10

(2) INFORMATION FOR SEQ ID NO:25:

(i) SEQUENCE CHARACTERISTICS:
        (A) LENGTH: 30 base pairs
        (B) TYPE: nucleic acid
        (C) STRANDEDNESS: double
        (D) TOPOLOGY: Not Relevant (ii) MOLECULE TYPE: DNA (genomic)

(ix) FEATURE:
        (A) NAME/KEY: misc_signal
        (B) LOCATION: 16..18

(ix) FEATURE:
        (A) NAME/KEY: CDS
        (B) LOCATION: 1..30

(xi) SEQUENCE DESCRIPTION: SEQ ID NO:25:

AAA ATT GTG GAT TTG GTC AAG GAG CTT GAC                            30
Lys Ile Val Asp Leu Val Lys Glu Leu Asp
1               5                  10

-continued (2) INFORMATION FOR SEQ ID NO:26:

(i) SEQUENCE CHARACTERISTICS:
        (A) LENGTH: 30 base pairs
        (B) TYPE: nucleic acid
        (C) STRANDEDNESS: double
        (D) TOPOLOGY: Not Relevant (ii) MOLECULE TYPE: DNA (genomic)

(ix) FEATURE:
        (A) NAME/KEY: CDS
        (B) LOCATION: 1..30

(xi) SEQUENCE DESCRIPTION: SEQ ID NO:26:

```
AAG ATA GTC GAC TTA GTG AAA GAA CTA GAA                              30
Lys Ile Val Asp Leu Val Lys Glu Leu Glu
             15                  20
```